(12) United States Patent
Amling et al.

(10) Patent No.: US 11,096,554 B2
(45) Date of Patent: Aug. 24, 2021

(54) MEDICAL SCOPE DEVICE WITH IMPROVED RADIO FREQUENCY DATA INTERFACE

(71) Applicant: KARL STORZ Imaging, Inc., Goleta, CA (US)

(72) Inventors: Marc R. Amling, Goleta, CA (US); Helga Schemm, Wurmlingen (DE); George E. Duckett, III, Castaic, CA (US); Eric Hale, Vancouver, WA (US)

(73) Assignee: KARL STORZ Imaging, Inc., Goleta, CA (US)

(*) Notice: Subject to any disclaimer, the term of this patent is extended or adjusted under 35 U.S.C. 154(b) by 64 days.

(21) Appl. No.: 16/751,501

(22) Filed: Jan. 24, 2020

(65) Prior Publication Data

US 2020/0154978 A1 May 21, 2020

Related U.S. Application Data

(60) Division of application No. 16/012,966, filed on Jun. 20, 2018, now Pat. No. 10,575,712, which is a continuation-in-part of application No. 15/598,196, filed on May 17, 2017, now Pat. No. 10,039,438, which is a continuation-in-part of application No. 15/161,007, filed on May 20, 2016, now Pat. No. 10,133,013.

(51) Int. Cl.
| | |
|---|---|
| *A61B 1/00* | (2006.01) |
| *A61B 1/06* | (2006.01) |
| *A61B 1/05* | (2006.01) |
| *A61B 1/045* | (2006.01) |
| *A61B 1/273* | (2006.01) |

(52) U.S. Cl.
CPC ...... *A61B 1/00016* (2013.01); *A61B 1/00013* (2013.01); *A61B 1/00029* (2013.01); *A61B 1/00117* (2013.01); *A61B 1/00124* (2013.01); *A61B 1/00128* (2013.01); *A61B 1/045* (2013.01); *A61B 1/05* (2013.01); *A61B 1/0684* (2013.01); *A61B 1/273* (2013.01)

(58) Field of Classification Search
CPC ............ A61B 1/00016; A61B 1/00013; A61B 1/00029; A61B 1/00117; A61B 1/00124; A61B 1/00128; A61B 1/045; A61B 1/05; A61B 1/0684; A61B 1/273
USPC .......................................................... 385/93
See application file for complete search history.

(56) References Cited

U.S. PATENT DOCUMENTS

| | | | | |
|---|---|---|---|---|
| 2011/0193948 A1* | 8/2011 | Amling | ............... | A61B 1/00059 348/68 |
| 2014/0320621 A1* | 10/2014 | Sonnenschein | ...... | A61B 1/0055 348/76 |
| 2016/0220324 A1* | 8/2016 | Tesar | ................. | G02B 21/0012 |

\* cited by examiner

*Primary Examiner* — Jerry M Blevins
(74) *Attorney, Agent, or Firm* — Michael Joseph Loi; David Noel Villalpando

(57) ABSTRACT

A medical camera system includes a video medical scope defining an enclosed space within a distal portion and a proximal portion that a user can attach and detach to each other. The two portions both have an interface for coupling to each other allowing radio frequency communications across a patient isolation barrier having improvements to avoid interfering with surrounding equipment. Power transfer elements provide for power transfer across the patient isolation barrier.

13 Claims, 27 Drawing Sheets

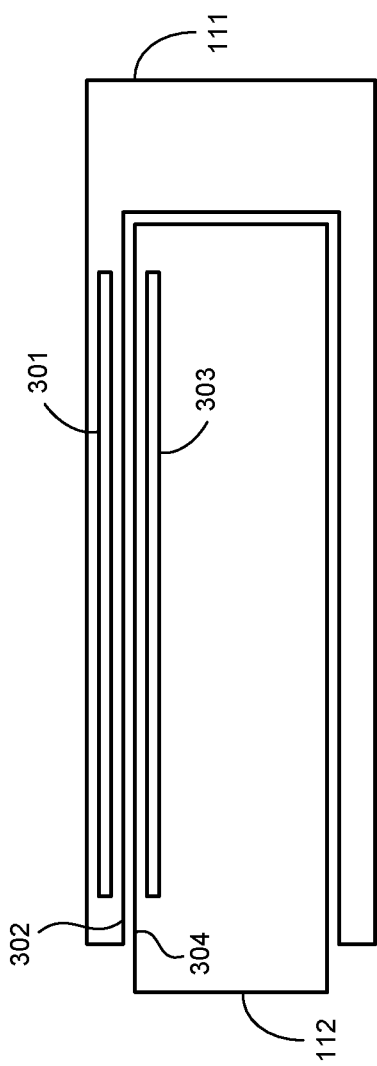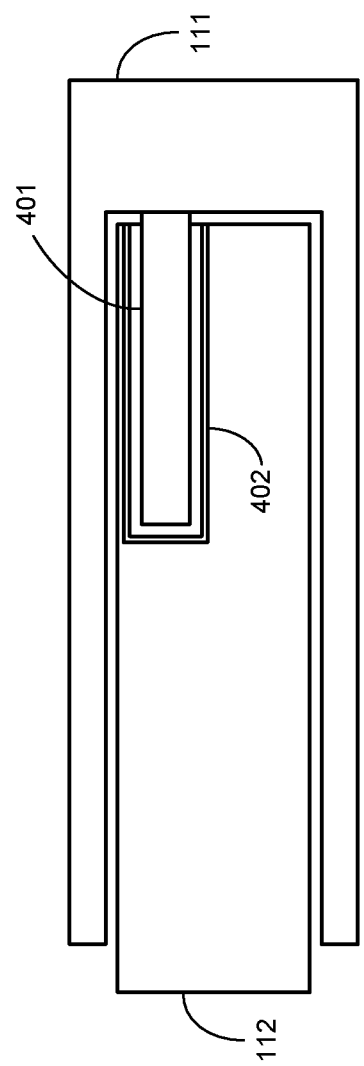
FIG. 3
FIG. 4

MEDICAL SCOPE DEVICE WITH IMPROVED RADIO FREQUENCY DATA INTERFACE

CROSS-REFERENCE TO RELATED APPLICATIONS

This application is a divisional of U.S. patent application Ser. No. 16/012,966, filed Jun. 20, 2018, and entitled, "Medical Scope Device with Improved Radio Frequency Data Interface," which is a continuation-in-part of U.S. patent application Ser. No. 15/598,196, filed May 17, 2017, now U.S. Pat. No. 10,039,438, issued Aug. 7, 2018, and entitled "Apparatus and Method of Providing An Interface To An Electrically Powered Instrument", which application is a continuation in part of Ser. No. 15/161,007, filed May 20, 2016, now U.S. Pat. No. 10,133,013, issued Nov. 20, 2018, and entitled "Apparatus and Method of Providing An Interface To An Electrically Powered Instrument"; and is related to co-pending continuation-in-part U.S. patent application Ser. No. 15/598,206, filed May 17, 2017, now U.S. Pat. No. 10,130,241, issued Nov. 20, 2018, and also entitled "Apparatus and Method of Providing An Interface To An Electrically Powered Instrument".

TECHNICAL FIELD OF THE INVENTION

The invention relates to electrical power and data interfaces with observation instruments, including optical instruments such as endoscopic devices. More particularly, the invention relates to connectors which are used to provide an interface between an electrically operated instrument and control or related equipment for the instrument. The invention also relates to methods for providing such an interface.

BACKGROUND OF THE INVENTION

Observation instruments, including optical instruments such as endoscopes, borescopes, and exoscopes may include an electronic imaging device located, for example, at the distal end of an elongated shaft or in a camera head which is connected to an elongated shaft. Whether positioned at the distal end of the endoscope shaft or in the camera head, the electronic imaging device may be one or more charge coupled devices (CCDs) or CMOS imaging devices together with other electronic components. Other electronic devices such as LED or other light sources may be included in the instrument. The camera head (or an instrument body or handle in the case of some observation instruments) is typically connected via a suitable cable to a camera control unit, commonly referred to as a "CCU." The cable provides paths for carrying electrical power to the camera head and data signals to and from the camera head. In particular, image data captured by the imaging device is transmitted over the cable to the CCU for processing and ultimately for display on monitors which are connected directly to the CCU or to an intermediate monitor driving device. Control signals and power for operating the electronic components in the instrument may be transmitted over the cable from the CCU to the scope and/or camera head.

It is known in the art to transmit data signals from an endoscope to a CCU in the form of optical signals rather than electrical signals. U.S. Publication 2015/0250378, for example, uses a cable between a camera head and CCU which includes optical fibers for carrying optical data signals from the camera head to the CCU. The camera head in this example includes circuitry for converting the captured image data from the electronic data signals generated by the imaging device to optical data signals which are then inserted into the optical fibers of the cable. U.S. Publication 2015/0250378 also discloses that the cable from the camera head to CCU may include electrical signal paths in addition to the optical signal paths.

U.S. Publication 2008/0225134 shows another endoscopic system having a cable between the CCU and camera head which includes both electrical signal paths and an optical path. In this case, the optical path is used to provide illumination light to the endoscope.

U.S. Publication No. 2014/0184771 teaches a camera system having a camera head with an imaging device and a first connector; a camera control unit with a processor and a second connector configured to removably engage the first connector; and wherein the first connector and the second connector are configured to allow for contactless transfer of data from the camera head to the camera control unit and contactless transfer of power from the camera control unit to the camera head.

U.S. Publication No. 2016/0089000 teach an endoscope which can perform non-contact electric power supply and non-contact signal transmission. A power receiving unit, an image signal transmission unit, and an endoscope side signal transmission and reception unit are disposed in the space (hollow structure) of a first connector of an endoscope. The first connector includes a first connector case and a second connector case disposed in order from a side of the second connector, and a division line between the first and second connector cases includes an inclined portion that is inclined with respect to an insertion direction of the first and second connectors.

Medical devices such as endoscopes require an electrical isolation barrier between the CCU and camera head/endoscope. This electrical isolation barrier is required to ensure that an inappropriate electrical signal is not inadvertently applied to the endoscope and thus to the patient in which the endoscope is used. Where a cable running between the CCU and endoscope includes electrical signal paths, such as in both of the above-mentioned U.S. patent application publications, it has been necessary for the electrical isolation barrier to be included in the circuitry of the CCU. This requirement of the electrical isolation barrier in the CCU greatly complicates the circuitry of the device. Further, the cable portion of a typical videoendoscope system is a relatively very expensive portion of the system and presents further difficulties in rotating the instrument during use.

SUMMARY OF THE INVENTION

It is an object of the invention to provide a medical camera system with improved communications across a patient isolation barrier. Another object of the invention is to provide a medical camera system allowing a proximal portion with a cable end to be disconnected from a distal portion with an image sensor, allowing interchangeability and disposability of distal portions. It is a further object in some embodiments of the invention to improve surgical procedures by allowing rotatability between a medical camera system proximal portion attached to a cable, and a distal portion having a shaft with an image sensor.

To achieve these objects, a medical camera system is provided including a video medical scope defining an enclosed space within a distal portion and a proximal portion that a user can attach and detach to each other. The two portions both have an interface for coupling to each other allowing communications across a patient isolation barrier. Power transfer elements provide for power transfer across the patient isolation barrier.

According to a first aspect of the invention, a video medical scope defining an enclosed space within a distal portion and a proximal portion, the video medical scope includes at least one image sensor for providing image data. A distal interface is arranged within the distal portion and includes a first radio frequency (RF) transmitter including a first RF antenna communicatively coupled to a first RF modulator and configured to transmit modulated image data beyond the enclosed space. The first RF antenna includes a short range low power RF antenna centrally located along the axis of rotation whereby the proximal portion and the distal portion rotate with respect to each other. The distal interface further includes a power receiving element for wirelessly receiving electrical. The proximal portion of the scope includes a proximal interface, with the distal and proximal interfaces adapted to releasably couple to each other and each interface lying on opposite sides of the enclosed space. The proximal interface includes a second RF antenna configured to receive the modulated image data from the first RF antenna. A first RF receiver is configured to receive the modulated image data from the second RF antenna. A power transmitting element is provided for wirelessly transmitting the electrical power when the first power transfer element is placed within a power coupling distance from the first receiving element. The first RF transmitter and first RF receiver are configured to provide a RF communication channel between the first RF transmitter and the first RF receiver when the distal and proximal interfaces are coupled.

In some implementations of the first aspect, the scope further includes a second RF modulator arranged within the proximal portion, the second RF modulator adapted to be communicatively coupled to a camera control unit (CCU) and configured to pass on control data for the image sensor from the CCU.

In some implementations of the first aspect, a first faraday cage structure is positioned surrounding the first RF antenna in all directions excepting the proximal direction, and a second faraday cage structure positioned surrounding the second RF antenna in all directions excepting the distal direction.

In some implementations of the first aspect, first RF antenna may be a directional antenna having a directional emission pattern directed toward the second antenna when the when the distal and proximal interfaces are coupled, and the second RF antenna is a directional antenna having a directional emission pattern directed toward the first RF antenna when the distal and proximal interfaces are coupled.

In some implementations of the first aspect, the first RF modulator and the first RF antenna make up a low power, near-field radio transmitter.

In some implementations of the first aspect, the proximal portion includes a first receptacle into which the distal portion is adapted to be partially inserted to couple the proximal and distal portions, the power transmitting element including an inductive coil positioned around an inside wall of the first receptacle, and the power receiving element including an inductive coil positioned along an outer edge of the distal portion.

In some implementations of the first aspect, the power transmitting element includes a first flat inductive coil positioned in a radial extension of the proximal portion, and the power receiving element including a second flat inductive coil positioned in a radial extension of the distal portion.

In some implementations of the first aspect, the distal portion contains an illumination light emitting device.

In some implementations of the first aspect, the proximal portion further includes a control data modulator coupled to the power transmitting element and adapted for transmitting control data to the distal portion via inductive coupling through the power transmitting element and the power receiving element.

According to a second aspect of the invention, a video medical scope is provided, the scope body defining an enclosed space within a distal portion and a proximal portion. The scope includes at least one image sensor for providing image data. A distal interface is arranged within the distal portion and including a first radio frequency (RF) transmitter including a first RF antenna communicatively coupled to a first RF modulator and configured to transmit the modulated image data beyond the enclosed space. A first faraday cage structure is positioned surrounding the first RF antenna in all directions excepting the proximal direction. A power receiving element is provided for wirelessly receiving electrical power. A corresponding proximal interface arranged within the proximal portion, with the distal and proximal interfaces arranged to be coupled to each other and each interface lying on opposite sides of enclosed space. The proximal interface includes a second RF antenna configured to receive the modulated image data from the first RF antenna. A second faraday cage structure is positioned surrounding the second RF antenna in all directions excepting the distal direction. A first RF receiver configured to receive the modulated image data from the second RF antenna. A power transmitting element is provided for wirelessly transmitting the electrical power when the first power transfer element is placed within a power coupling distance from the first receiving element. The first RF transmitter and first RF receiver are configured to provide a RF communication channel between the first RF transmitter and the first RF receiver.

In some implementations of the second aspect, the first RF antenna includes a short range low power RF antenna centrally located along the axis of rotation whereby the proximal portion and the distal portion rotate with respect to each other.

In some implementations of the second aspect, the first RF antenna is a directional antenna having a directional pattern pointing toward the second antenna when the when the distal and proximal interfaces are coupled, and the second RF antenna is a directional antenna having a directional pattern pointing toward the first RF antenna.

In some implementations of the second aspect, the first RF modulator and the first RF antenna make up a low power, near-field radio transmitter.

In some implementations of the second aspect, the proximal portion includes a first receptacle into which the distal portion is adapted to be partially inserted to couple the proximal and distal portions, the power transmitting element including an inductive coil positioned around an inside wall of the first receptacle, and the power receiving element including an inductive coil positioned along an outer edge of the distal portion.

In some implementations of the second aspect, the power transmitting element includes a first flat inductive coil positioned in a radial extension of the proximal portion, and the power receiving element includes a second flat inductive coil positioned in a radial extension of the distal portion.

In some implementations of the second aspect, the distal portion contains an illumination light emitting device.

In some implementations of the second aspect, the proximal portion further includes a control data modulator coupled to the power transmitting element and adapted for transmitting control data to the distal portion via inductive coupling through the power transmitting element and the power receiving element.

According to a third aspect of the invention, a video medical scope is provided defining an enclosed space within a distal portion and a proximal portion. The scope includes at least one image sensor for providing image data. A distal interface is arranged within the distal portion and including a first radio frequency (RF) transmitter including a first RF antenna communicatively coupled to a first RF modulator and configured to transmit modulated image data beyond the enclosed; the distal interface further including a power receiving element for wirelessly receiving electrical power. A proximal interface is arranged within the proximal portion, the distal and proximal interfaces are adapted to releasably couple to each other and each interface lying on opposite sides of the enclosed space, the proximal interface including a second RF antenna configured to receive the modulated image data from the first RF antenna. The proximal portion includes a first RF receiver configured to receive the modulated image data from the second RF antenna, and a power transmitting element for wirelessly transmitting the electrical power when the first power transfer element is placed within a power coupling distance from the first receiving element. The first RF transmitter and first RF receiver are respectively configured to provide a RF communication channel between the first RF transmitter and the first RF receiver when the distal and proximal interfaces are coupled. The first RF antenna is a directional antenna having a directional emission pattern directed toward the second antenna when the when the distal and proximal interfaces are coupled, and the second RF antenna is a directional antenna having a directional emission pattern directed toward the first RF antenna when the distal and proximal interfaces are coupled.

In some implementations of the third aspect, the scope further includes a first faraday cage structure positioned surrounding the first RF antenna in all directions excepting the proximal direction, and a second faraday cage structure positioned surrounding the second RF antenna in all directions excepting the distal direction.

In some implementations of the third aspect, the first RF modulator and the first RF antenna include a low power, near-field radio transmitter, and first RF receiver and the second RF antenna include a low power, near-field radio receiver.

These and other advantages and features of the invention will be apparent from the following description of representative embodiments, considered along with the accompanying drawings.

BRIEF DESCRIPTION OF THE DRAWINGS

FIG. 3 is a schematic representation showing a power transfer element arrangement according to one embodiment of the invention.

FIG. 4 is a schematic representation showing a power transfer element arrangement according to another embodiment of the invention.

Like numbers generally indicate like elements in the drawings.

DESCRIPTION OF REPRESENTATIVE EMBODIMENTS

The present invention is disclosed below in the context of an endoscopic system. Embodiments also include apparatus and methods for other electrically powered instruments. Thus, optical instruments (e.g., video cameras, endoscopes, exoscopes, borescopes) employing high-resolution imaging (e.g., a 4K resolution design) is an illustrative, but non-limiting example embodiment. More generally, an interface or connector within the scope of the following claims may have application in connection with any observation instrument.

Figure 1:
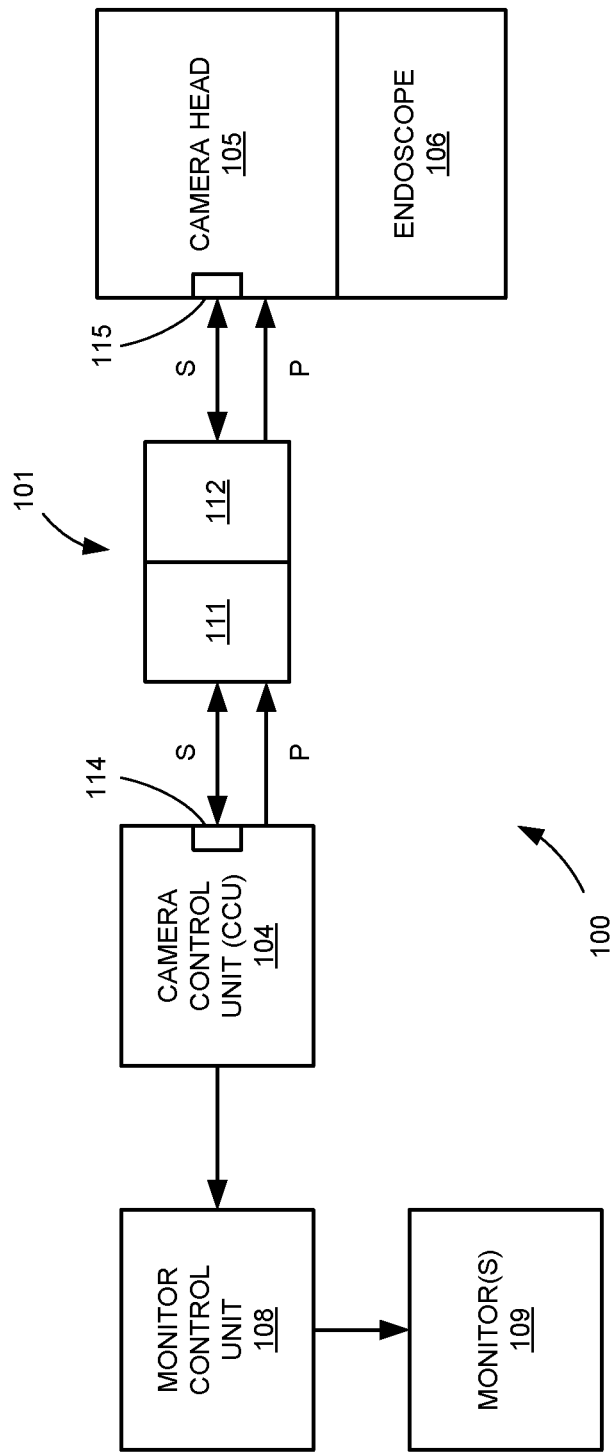
FIG. 1 is a block diagram showing an endoscopic system incorporating an interface device according to an aspect of the present invention.

FIG. 1 shows an endoscopic system 100 employing an interface device 101 according to the present invention. System 100 includes a camera control unit ("CCU") 104, a camera head 105, and an endoscope 106. CCU 104 is connected to send a signal to a monitor control unit 108 connected to monitors 109 for displaying images from camera head 105 or endoscope 106.

Interface device 101 is interposed between CCU 104 and camera head 105 and functions as a detachable link for data communication and power transfer between the CCU and camera head. Both the data communication and power transfer functions are preferably provided across interface device 101 while the device also maintains an electrical isolation barrier to camera head 105 and endoscope 106. Data is communicated in the form of optical data signals S in FIG. 1, both from camera head 105 and/or endoscope 106 to CCU 104 and also preferably in the opposite direction from the CCU to the camera head and/or endoscope. Electrical power (P in FIG. 1) is transferred only in the direction from CCU 104 to camera head 105 and/or endoscope 106. The data transmission rates possible via optical data transmission in the direction from the camera head 105 to CCU 104 is particularly advantageous for transmitting the large amounts of image data that may be collected by an imaging device or multiple imaging devices (not shown) associated with endoscope 106 or camera head 105. Data which may be transmitted from CCU 104 to camera head 105 and/or endoscope 106 may include control instructions and operational instructions and data, which may typically be of lesser volume as compared to the image data transmitted in the opposite direction.

Interface device 101 includes a first connector 111 and a second connector 112 which may be connected in an operating position to facilitate the desired data communication and power transfer. This operating position is schematically indicated in FIG. 1 and will be described in further detail below with reference particularly to FIGS. 2 and 9. The two connectors 111 and 112 may be readily separated to detach camera head 105 and endoscope 106 from CCU 104 and then reconnected in the operating position as desired. For example, connector 112 may be detached from connector 111 in preparation for sterilizing camera head 105 and/or endoscope 106. Once the sterilization or other process or activity requiring detachment is complete, connectors 111 and 112 may be readily connected back together again in the operating position to again facilitate data communication and power transfer between CCU 104 and camera head 105/endoscope 106.

The position of interface device 101 shown in FIG. 1 between CCU 104 and camera head 105 is intended to indicate that the device may be interposed at any position between those two devices. One embodiment that will be described further below in connection with FIGS. 2 and 6-9 incorporates first connector 111 in a housing for CCU 104. In this embodiment, first connector 111 may be formed as a receptacle in a housing for CCU 104 and adapted to receive second connector 112 in the operating position. Second connector 112 in this embodiment is connected to a suitable cable having optical conduits such as optical fibers for carrying the optical signals and suitable conductors for conducting electrical power to camera head 105. Such a cable will be described below in connection with FIG. 5. However it should be borne in mind that the invention is not limited to this arrangement in which one of the connectors is incorporated in the CCU or one of the other devices in the system.

Before moving on to describe further details of interface device 101, it should be noted that both CCU 104 and camera head 105 include components for supporting the interface. In particular, CCU 104 includes a signal conversion unit 114 to convert incoming optical signals from the direction of camera head 105 to electrical signals for further processing and to convert electrical signals generated at the CCU to optical signals for transmission to the camera head and/or endoscope 106. Similarly camera head 105 includes a signal conversion unit 115 for converting image data and other signals to optical signals for transmission to CCU 104 and for converting incoming optical signals from the CCU 104 to electrical signals for use in the camera head 105 or endoscope 106.

Figure 2:
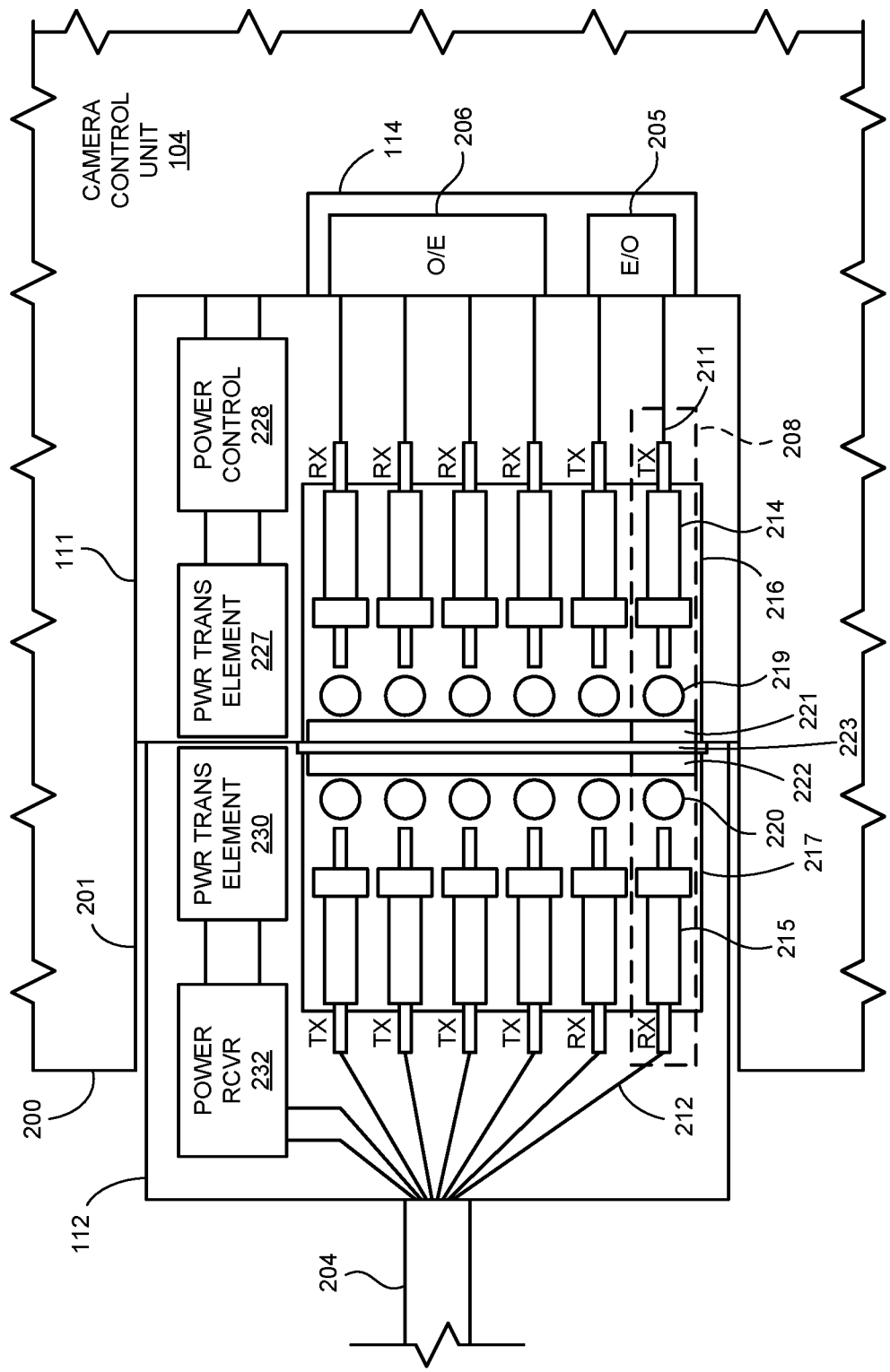
FIG. 2 is a schematic diagram of the interface device shown in FIG. 1.

FIG. 2 shows an embodiment of interface 101 with first connector 111 incorporated in a housing 200 for CCU 104. First connector 111 defines a receptacle 201 in CCU housing 200 which is adapted to receive second connector 112 in the operating position shown in the figure. Second connector 112 in this illustrated embodiment is connected to a cable 204 which includes elements for carrying the optical signals and electrical signals to camera head 105 shown in FIG. 1. Further details of a suitable cable will be described below with reference to FIG. 5.

In order to support the optical data signal communications through interface 101, CCU 104 includes signal conversion unit 114. Signal conversion unit 114 includes an electro-optical converter 205 for converting electrical signals from CCU 104 to optical signals for transmission in the direction to camera head 105. Signal conversion unit 114 also includes an opto-electrical converter 206 for converting optical signals received from camera head 105 and/or endoscope 106 to electrical signals for processing in other elements (not shown) of CCU 104. The electro-optical converter 205 and opto-electrical converter 206 included in signal conversion unit 114 are well known in the art. Thus these signal conversion elements will be described herein only generally so as not to obscure the present invention in unnecessary detail.

The embodiment shown in FIG. 2 includes six different optical signal paths. A portion of one such optical signal path is shown within dashed box 208 in FIG. 2. Each optical signal path is defined in part by a first optical fiber 211 associated with first connector 111 and a second optical fiber 212 associated with second connector 112. First optical fiber 211 terminates in connector 111 in a suitable ferrule 214, while second optical fiber 212 terminates in connector 112 in a corresponding ferrule 215. Each ferrule 214 in connector 111 is mounted in an alignment block 216 mounted in that connector. Similarly, each ferrule 215 in connector 112 is mounted in an alignment block 217 mounted in that connector. Each alignment block 216 and 217 is positioned to align with the opposite alignment block when connectors 111 and 112 are in the illustrated operating position so as to align the terminating end of each optical fiber 211 with the terminating end of the corresponding fiber 212 in the respective optical signal path.

Each optical signal path in this illustrated form of the invention also includes an expanded beam coupling arrangement for coupling the optical signal carried through one fiber 211 or 212 to the optical fiber included with the opposite connector. The expanded beam arrangement for a given optical signal path includes an optical lens 219 aligned with the terminating end of optical fiber 211, and an optical lens 220 aligned with the terminating end of optical fiber 212. Optical lens 219 for an incoming optical signal from fiber 211 in the lowermost optical signal path shown in dashed box 208 in FIG. 2 is operable to expand and collimate the incoming optical signal to distribute the optical power of the signal over a larger area (larger than the fiber) within the coupling region defined between the two lenses 219 and 220. On the opposite side of the interface along the lowermost signal path, optical lens 220 serves to focus the expanded beam back down to the area defined by the terminating end of optical fiber 212 in which the signal is to be inserted. Thus the arrangement of operatively aligned fiber 211 and optical lens 219, and corresponding operatively aligned fiber 212 and optical lens 220 along a given optical path provides an optical coupling that couples a light signal exiting one of the fiber ends into the end of the corresponding fiber.

It should be noted here that although the representative embodiment shown in FIG. 2 and embodiments described below in connection with FIGS. 6-9 show ball lenses for lenses 219 and 220, the present invention is not limited to embodiments using ball lenses. Other embodiments may employ GRIN lenses, aspherical lenses, or drum lenses with spherical surfaces, for example. Also, although the various elements of an optical signal path are labeled in FIG. 2 only for the path in dashed box 208. The reference signs for the path in dashed box 208 apply to the corresponding elements of the other five optical signal paths.

First connector 111 and second connector 112 each includes a suitable protective transparent cover extending transverse to each signal path. The protective cover for first connector 111 is shown at 221 in FIG. 2, while the protective cover for second connector 112 is shown at 222. Protective covers 221 and 222 may comprise Sapphire or any other suitable material and forms an exterior surface of the respective connector covering the adjacent optical lens. This arrangement protects optical lenses 219 and 220 from damage when connectors 111 and 112 are not connected in the operating position shown in FIG. 2.

In the embodiment of the invention shown in FIG. 2, first and second connectors 111 and 112, respectively, are configured to leave an air gap 223 between covers 221 and 222 when the connectors are connected together in the operating position. Each optical signal path, such as the path shown in dashed box 208, includes a portion traversing this air gap 223. Air gap 223 is used to prevent contact between the covers 221 and 222, and may be very narrow, on the order of 1 mm or less. It will be appreciated that other embodiments of the connectors 111 and 112 may be configured so that there is essentially no air gap between covers 221 and 222. Rather, the outer surfaces of covers 221 and 222 may abut each other when connectors 111 and 112 are connected together in the operating position.

The example provided in FIG. 2 shows four optical paths (the upper four in the figure) dedicated for optical transmissions in the direction from camera head 105 to CCU 104. These optical transmissions (in the illustrated use in an endoscopic system 100 in FIG. 1) will include image data which may include a very large volume of data depending upon the resolution of the imaging device associated with camera head 105 or endoscope 106 and on other factors. In this example, two optical paths (the lower two in FIG. 2) are dedicated for the transmission of optically encoded data in the direction from CCU 104 to camera head 105. This data may include instructions and control signals for camera head 105 and/or endoscope 106. It should be appreciated that the invention is not limited to any particular number of optical paths or any particular optical encoding technique. Although FIG. 2 suggests that each optical signal path accommodates only unidirectional data transmission, other embodiments may include bidirectional transmission over each optical path. Also, various optical signal encoding techniques may be employed to further increase the rate at which data may be transmitted through interface 101. For example wave division multiplexing techniques or other multiplexing techniques may be used to transmit multiple different data streams contained in a single multiplexed signal across a given optical signal path. Of course the receiving and transmitting elements in CCU 104 and camera head 105 must support the respective encoding and transmission technique employed across the optical signal paths. For example, signal multiplexing techniques employ a multiplexer at the transmission side and a demultiplexer at the receiving side.

Interface 101 shown in FIG. 2 also includes an arrangement for wirelessly transferring power from first connector 111 on the CCU side of the interface to second connector 112 on the camera head side of the interface. This electrical power supplied to camera head 105 and/or endoscope 106 is necessary for operating electronic elements included in the camera head and endoscope. For example, the electrical power may be used to operate an imaging device and related electronic components in camera head 105 or endoscope 106, opto-electrical and electro-optical converters associated with the camera head, and illumination elements (not shown in the figures) associated with the camera head and/or endoscope. The wireless power transfer arrangement includes a first power transfer element 227 included with first connector 111, and a power control circuit 228 connected to the first power transfer element. A second power transfer element 230 is included with second connector 112 together with a power receiver or conditioner 232. When the two connectors 111 and 112 are connected in the operating position indicated in FIG. 2, the two power transfer elements 227 and 230 are in a power transfer orientation with respect to each other, which, in this embodiment comprises an orientation in which the power transfer elements are inductively coupled. Power control circuit 228 is operable to supply a suitable driving signal to cause a variable current flow in first power transfer element 227 and consequent electromagnetic field around the first power transfer element. This field produced around first power transfer element 227 induces a current in second power transfer element 230. The induced current is conditioned by power receiver/conditioner circuit 232 to provide a suitable power signal for transmission to the camera head over electrical conductors included in cable 204. For example, power receiver/conditioner circuit 232 may comprise a suitable rectifying circuit for converting the signal induced in second power transfer element 230 to a DC voltage signal suitable for use by electronic components included in camera head 105 and endoscope 106 (shown in FIG. 1).

This preferred arrangement of wireless power transfer between connectors 111 and 112 results in complete electrical isolation between electrical circuits associated with the first connector and electrical circuits associated with the second connector. Thus interface 101 itself made up of connectors 111 and 112 provides the required electrical isolation barrier between CCU 104 and camera head 105/endoscope 106. This electrical isolation barrier included in interface 101 obviates the need for an electrical isolation barrier in the circuitry of CCU 104, which is typically complicated and serves as a constraint on CCU design.

It should be appreciated that although the wireless power transfer arrangement across connectors 111 and 112 represents a preferred form of the present invention, alternative embodiments may include a contact-type power transfer arrangement which relies on electrical contacts in the connectors. In this alternative arrangement the first power transfer element comprises a pair of electrical contacts (positive and negative) associated with one connector while the second power transfer element comprises a corresponding pair of electrical contacts associated with the other connector. The like polarity contacts in these two pairs of electrical contacts would simply make contact with each other when connectors 111 and 112 are connected in the operating position. This contacting position represents the power transfer orientation in this contact-type embodiment. Of course, the contact-type embodiments do not provide the electrical isolation provided by the embodiment shown in FIG. 2. Thus a system such as system 100 in FIG. 1 employing a data and power interface having a contact-type power transfer arrangement would have to provide an electrical isolation barrier outside of the interface.

FIGS. 3 and 4 show alternative arrangements for first and second power transfer elements, 227 and 230, respectively, shown in FIG. 2. The high-level schematic diagram of FIG. 3 shows that the first and second power transfer elements may each comprise a suitable planar spiral coil. In particular, a first planar spiral coil 301 comprises the power transfer element associated with first connector 111, and is aligned with its plane parallel to a first side 302 of that connector. This side 302 forms an inner surface of the receptacle defined by first connector 111 in this example. A second planar spiral coil 303 comprising the power transfer element associated with second connector 112 is mounted parallel to a side surface 304 of that connector. When first connector 111 and second connector 112 are placed in the operating position indicated in FIG. 3, the spiral coil 301 comprising the first power transfer element aligns with the spiral coil 303 comprising the second power transfer element so that the two coils are inductively coupled.

The high-level schematic diagram in FIG. 4 shows an alternative arrangement in which a helical coil 401 comprises the power transfer element associated with the first connector 111. This helical coil 401 protrudes from first connector 111 into the area defined by the receptacle of the first connector. A second helical coil 402 comprises the power transfer element associated with second connector 112. Helical coil 402 in this embodiment has a diameter large enough to receive helical coil 401. When first connector 111 and second connector 112 are placed in the operating position with the second connector received in the receptacle defined by the first connector, helical coil 401 comprising the first power transfer element aligns with and extends into helical coil 402 comprising the second power transfer element so that the two coils are inductively coupled to facilitate the desired power transfer. Of course other arrangements within the scope of the present invention may reverse the helical coils so that a helical coil on connector 112 extends into the area defined by a larger diameter helical coil on connector 111.

Figure 5:
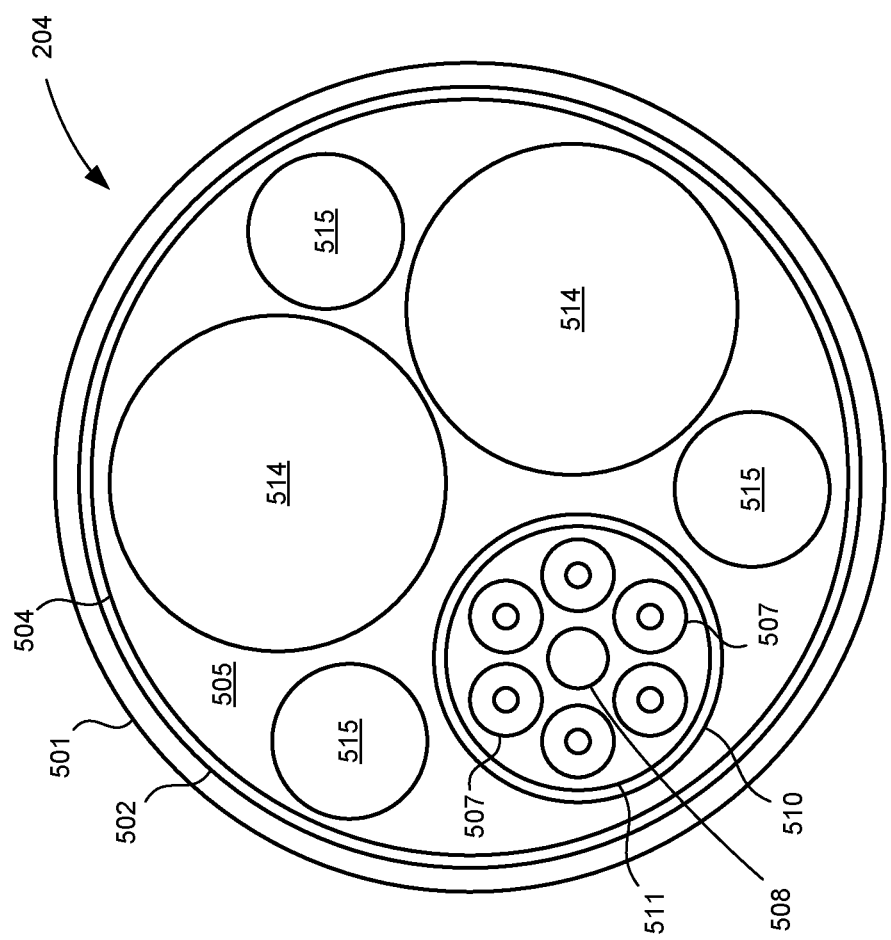
FIG. 5 is a schematic representation of a cross-section of a cable that may be employed with the interface device shown in FIG. 2.

The schematic representation of FIG. 5 shows a cable structure which may be employed for cable 204 shown in FIG. 2. In this example, cable 204 includes a cover material 501 lined inside by a moisture protection layer 502 and an EMF shielding layer 504. These three layers 501, 502, and 504 define and interior area 505 for optical fibers, electrical conductors, and reinforcing elements as desired. In particular, interior area 505 provides room for six optical fibers 507, which, together with a filler or reinforcing element 508 are grouped together in a mono coil 510 lined with a suitable protective layer 511. Area 505 also provides room for two conductors 514 (separate power and ground conductors) which may comprise sheathed AWG 26 copper wire for example. The example of FIG. 5 also shows three strands of filler/reinforcement 515. It will be appreciated that optical fibers 507 shown in FIG. 5 comprise the continuation of fibers 212 which terminate in second connector 112 in FIG. 2. Conductors 514 terminate in second connector 112 shown in FIG. 2 at power receiver/conditioner 232.

This cable arrangement shown in FIG. 5 has the advantage that the bundle of optical fibers may be readily changed as desired by simply pulling the fiber 507 and filler/reinforcement strand 508, and replacing that bundle with another bundle having more or fewer fibers. Cable 204 shown in FIG. 5 may also be modified by using the conductive mono coil 510 and the EMF shielding 504 to replace the two copper conductors 514. This allows the cable to have a smaller diameter, or allows the area taken up by conductors 514 to be used for additional optical fibers, preferably run in one or more additional mono coils. In any event, the combination of optical fiber transmission elements together with the electrical conductors allows the cable to support the optical data transmission and electrical power transfer facilitated by interface 101.

Figure 6:
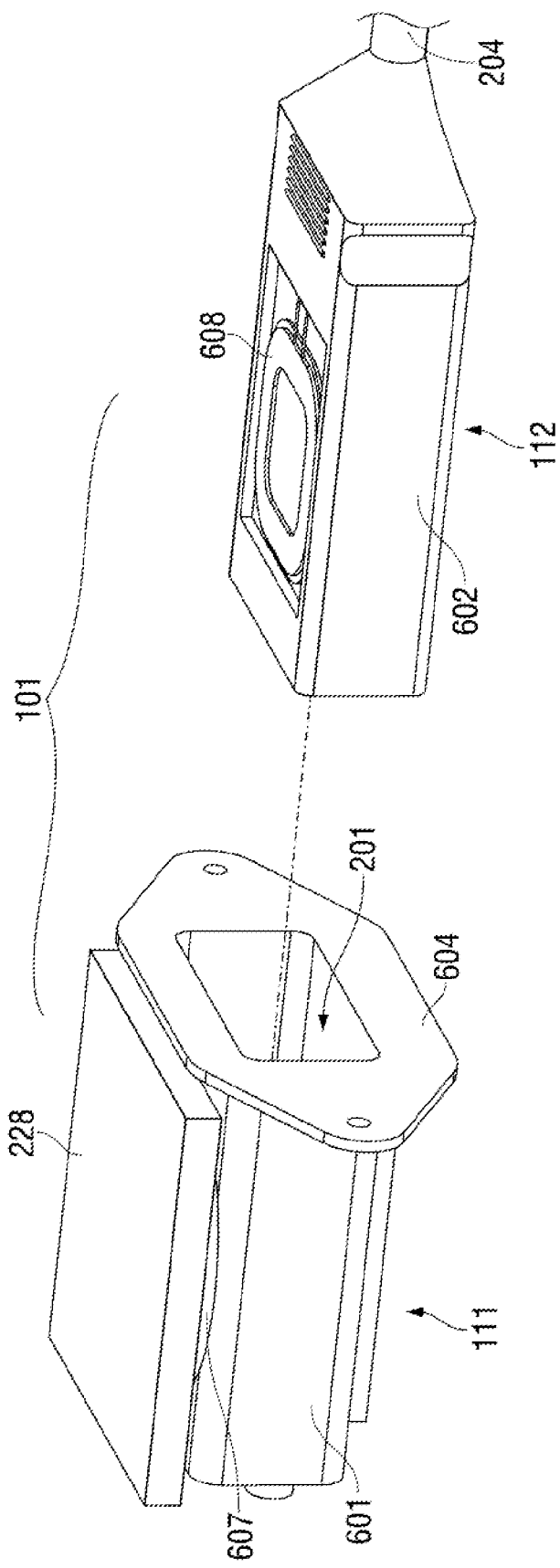
FIG. 6 is a view in perspective showing a pair of connectors making up an interface device according to an embodiment of the invention.

FIGS. 6 through 9 show an example of an interface device 101 in which first connector 111 is adapted to be incorporated with the housing of another component such as CCU 104 shown in FIG. 1. As shown in FIG. 6, first connector 111 includes a housing 601 while second connector 112 includes a housing 602. Housings 601 and 602 each provide an enclosure for components of the respective connector. Housing 601 also includes a flange 604 by which first connector 111 may be secured to a component such as CCU 104 in FIG. 1. Housing 601 also defines a receptacle 201 in which housing 602 for connector 112 can be inserted to place the two connectors in the operating position. Second connector 112 is connected to cable 204 which extends to a camera head or endoscope such as those described above.

Figure 7:
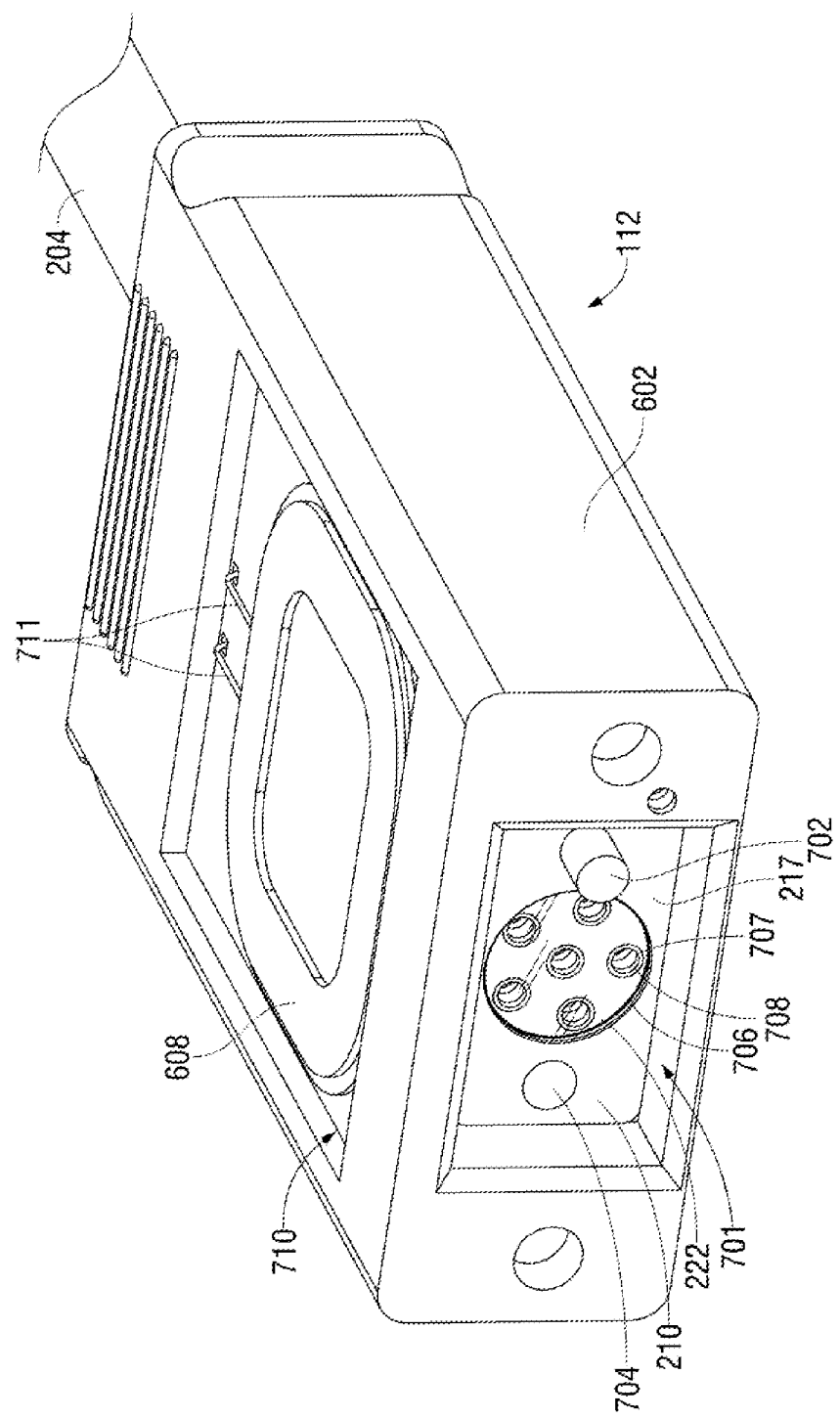
FIG. 7 is a view in perspective showing an end of one of the connectors shown in FIG. 6.

The perspective of FIG. 7 shows an end of connector 112 which is received in receptacle 201 defined by housing 601 in FIG. 6 when the connectors are brought together in the operating position. This end of connector 112 includes a recess 701 in which the alignment block 217 of connector 112 is mounted. An alignment pin 702 projects from a face of alignment block 217, while an alignment pin receiver opening 704 is also located on the face of the alignment block. A recess 706 for receiving protective cover 222 is formed between alignment pin 702 and alignment pin receiver 704. An end of the portion of each optical signal path in connector 112 is visible in FIG. 7 within the area of recess 706 behind the transparent protective cover 222. Each such end is defined by a circular opening 707. A lens retainer 708 is apparent in each such circular opening in the perspective of FIG. 7, although components within each optical signal path are not visible in this view. Components within each optical signal path are, however, shown in the section view of FIG. 9, as will be described below.

Figure 8:
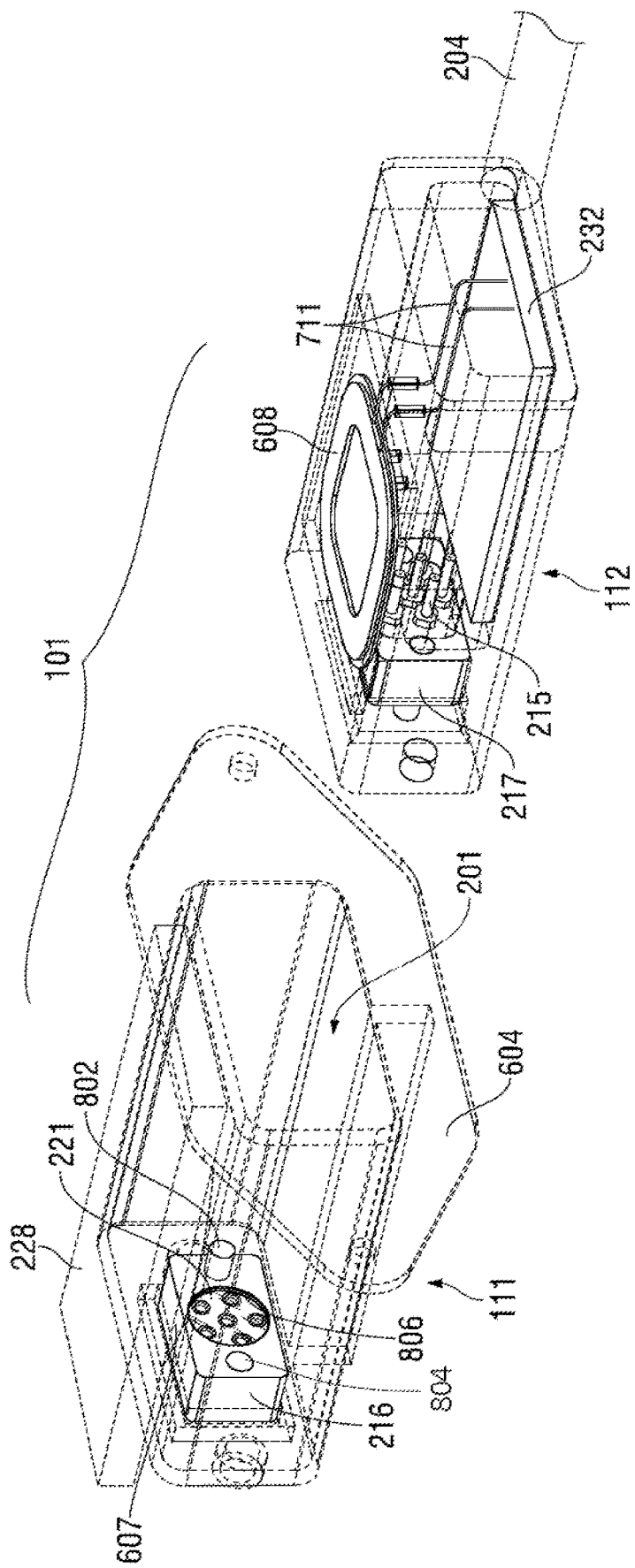
FIG. 8 is a view in perspective similar to FIG. 6, but showing the housing of each connector and certain other features in dashed lines to show the internal components of the connectors and their position relative to the respective housing.

FIG. 8 shows both connectors 111 and 112 aligned so that they may be brought together in the operating position. The connector housings (housing 601 and 602) are shown in dashed lines in FIG. 8 (as are power control circuit 228 and coil 607 for connector 111) so that the internal components of each connector are visible. The internal components of each connector are also shown in the section view of FIG. 9 which is taken along a vertical plane through the center longitudinal axis of the connectors 111 and 112 in the operating position.

Figure 9:
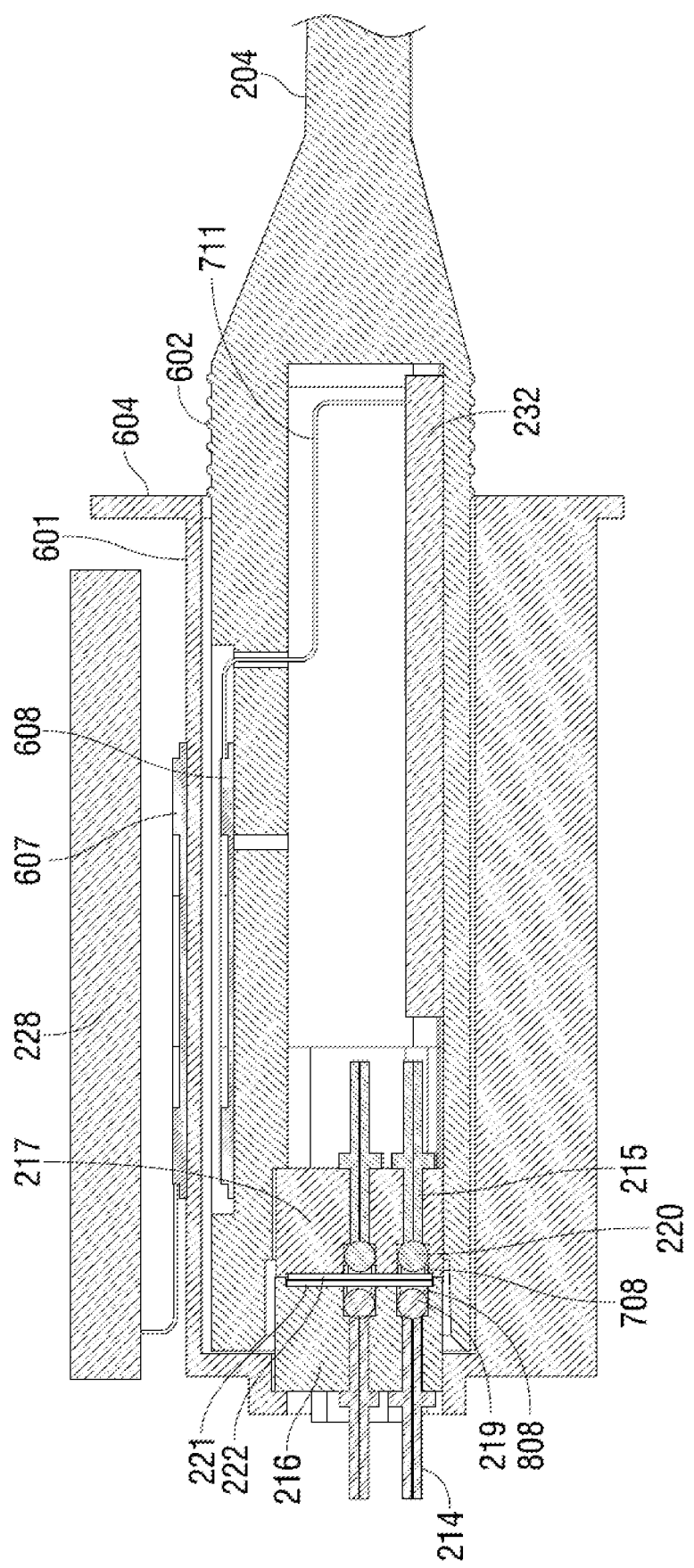
FIG. 9 is a view in section though the connectors shown in FIGS. 6 and 8 in an operating position, the section being taken along a vertical plane through the center longitudinal axis of the connectors.

FIGS. 8 and 9 show alignment block 216 for connector 111 and alignment block 217 for connector 112. As is apparent from FIG. 8, alignment block 216 includes a complementary structure to alignment block 217 with an alignment pin 802 and an alignment pin receiver opening 804. When the two connectors 111 and 112 are brought together in the operating position shown in FIG. 9, the alignment pin of one alignment block is received with close tolerance in the alignment pin receiver opening of the opposite alignment block. This alignment arrangement helps ensure proper alignment of the respective portions of the optical paths formed by the two connectors. As shown in FIG. 8, alignment block 216 also includes a recess 806 in which is mounted transparent protective cover 221. An end of each optical path portion in connector 111 is also visible through the transparent protective material as circular openings although these circular openings are not labeled in the figure in view of the scale of the drawing.

A rear side of alignment block 217 in connector 112 is visible in the view of FIG. 8. This rear side is the side opposite the side shown in the view of FIG. 7. The ferrules 215 for alignment block 217 are visible in FIG. 8, while the section view of FIG. 9 shows two of the ferrules associated with both alignment blocks, namely, ferrules 214 in alignment block 216 and ferrules 215 in alignment block 217. The section view of FIG. 9 also shows the optical lenses 219 and 220, lens retainers 708 and 808, and protective cover material 221 and 222 associated with two of the optical paths defined through the connectors in the operating position.

The example interface device 101 shown in FIGS. 6-9 employs a circular arrangement of ferrules in each alignment block (216, 217). That is, the arrangement includes five ferrules arranged in a circle with the sixth ferrule in the center of that circular shape. The circular arrangement is desirable because it makes efficient use of space in the alignment blocks. However, ferrules may be arranged in any pattern in an alignment block in embodiments of the invention to suit the given application.

It should be noted here that both FIGS. 8 and 9 omit the optical fibers which would be included in connectors 111 and 112 (as shown in FIG. 2) and also omit the electrical conductors extending from circuits 228 and 232. The fibers and conductors are omitted from these views in order to better show the remaining structure of the connectors. Those familiar with optical fiber connections will appreciate that the respective fiber received in a given one of the ferrules 214 or 215 would be positioned so that its end is effectively optically coupled to the respective lens 219 or 220. The fiber may or may not abut the lens depending upon the properties of the lens. In connector 112 each fiber would extend away from its respective ferrule and into cable 204. Each fiber in connector 111 would extend from the respective ferrule to the signal conversion unit associated with that connector (such as conversion unit 114 shown in FIGS. 1 and 2).

The embodiment shown in FIGS. 6-9 includes a power transfer arrangement in which the two connectors 111 and 112 are electrically isolated from each other and power is transferred via an inductive coupling. The inductive coupling in this case is between planar spiral coils. Coil 608 is included on connector 112 and mounted with its plane parallel to a top side of housing 602 in the orientation of the figure. Although it is largely obscured in FIG. 6 by power control circuit 228, connector 111 includes a corresponding spiral coil 607. Coil 607 is mounted outside of receptacle 201 with its plane extending parallel to a top side of the connector in the orientation of the figure. As will be described further below in connection particularly with FIG. 9, these locations of the coils 607 and 608 facilitate the desired inductive coupling when the connectors are in the operating position.

FIG. 7 shows that coil 608 is mounted in a top recess 710 in connector housing 602 so that the coil does not protrude from an uppermost plane of the connector. Conductors 711 extend to the power receiving/conditioning circuit 232 (shown in FIG. 8) inside housing 602. Although this recessed arrangement for coil 608 is preferred, other forms of the invention may use a planar coil that is mounted on top of the top surface of housing 602 so that the coil protrudes somewhat from that surface.

FIG. 9 shows that the two coils are aligned for inductive coupling when the connectors are placed in the operating position. In particular, the position of each coil in its respective connector allows the two coils to reside essentially parallel to each other and in alignment when the connectors are placed in the operating position. This alignment of coils 607 and 608 produces an inductive coupling between the two coils to allow transfer of electrical power from connector 111 to connector 112 as described above.

Regardless of the power transfer arrangement that may be used in a given embodiment of the present invention, and regardless of the number of optical signal paths employed for data communications across interface device 101, connectors 111 and 112 will be held securely together in the operating position in order to form the desired interface. Any suitable technique or combinations of arrangements may be used within the scope of the invention to secure connectors 111 and 112 in the desired operating position to facilitate power transfer and data communication, but allow the connectors to be readily separated as desired. For example, detents may be included on the exterior of one connector and cooperate with corresponding projections on the opposite connector to retain connectors 111 and 112 in the desired operating position. In another arrangement, one connector may include a locking feature such as a suitable ridge and the other connector may include a cooperating latch piece adapted to reside in either a locking position in which it contacts the locking feature to retain the connectors in the operating position, or a release position in which the connectors may be separated. In the example of FIGS. 6-9, the alignment pins 702 and 802 and alignment pin receiving openings 704 and 804 may be formed from suitable material and sized to provide a friction fit which holds the two connectors together once in the operating position until a suitable separating force is applied to separate the connectors.

Figure 10:
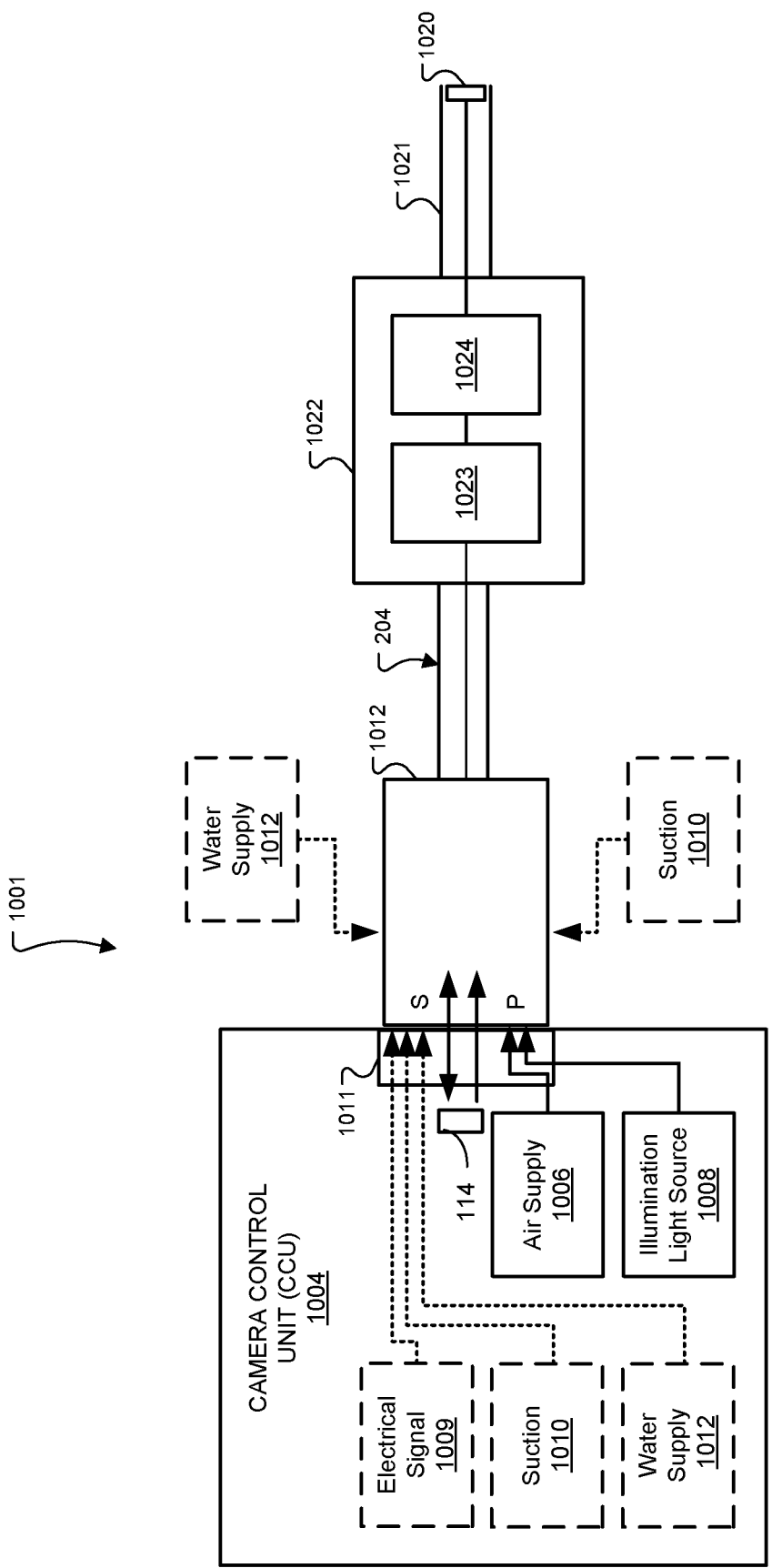
FIG. 10 is a block diagram of another embodiment of a system including two connectors.
Figure 11:
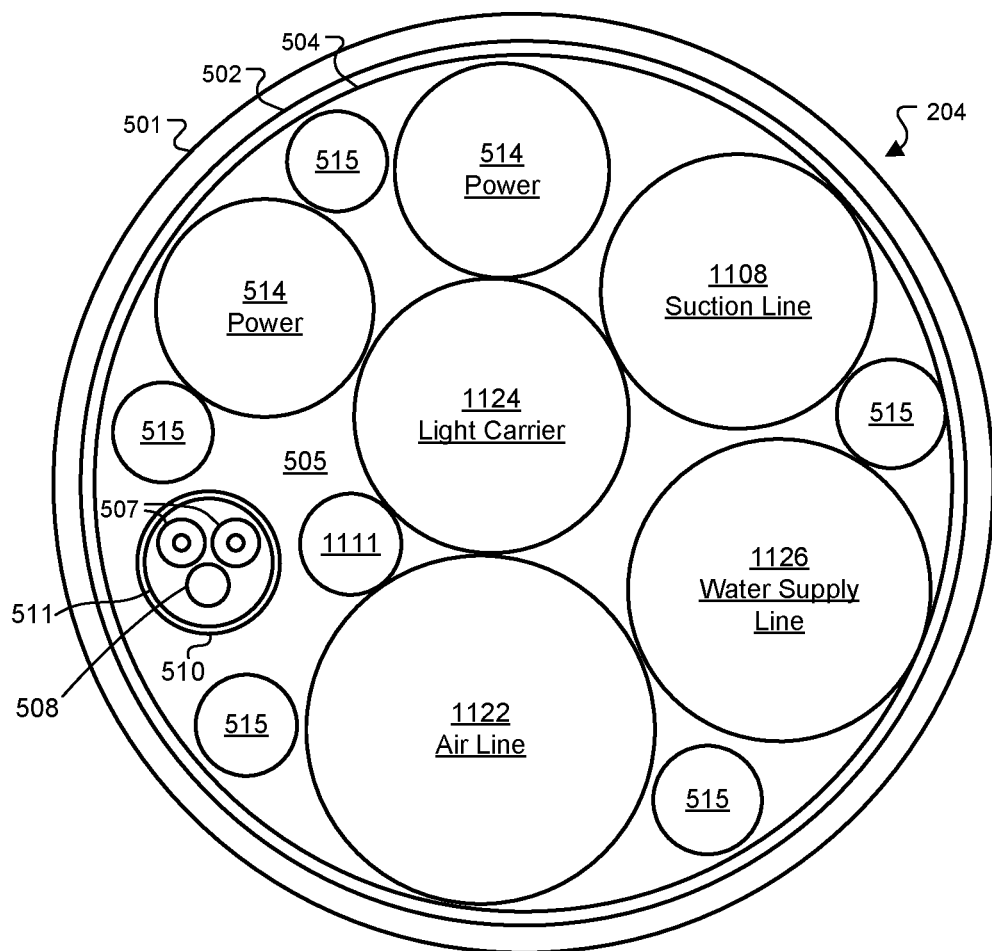
FIG. 11 is a cross section diagram of another example cable.

FIG. 10 is a block diagram of another embodiment of a system including two connectors. In this version, a gastrointestinal (GI) endoscope is connected to a CCU or other device 1004 using connectors 1011 and 1012 to cable 204 for connection to a GI endoscope 1022. The cable 204 may also carry air or insufflation gasses, a water line, and a suction line as seen in FIG. 11 for use in GI scope procedures. The CCU 1004 may be a CCU, a light source, a combination of modular components, or a combined control module (combi-box) including an internal air supply module 1006, and an illumination light source 1008. These may also be external to the CCU 1004 but connected to ports or channels provided on the combi-box for supplying the respective channels to first connector 1011. While various versions of a CCU are described here, another device such as a light supply or other modular device for a medical system may be placed at the position shown for CCU 1004, which may connect by a wired or wireless connection to a CCU or other imaging controller associated with the scope. An electrical signal 1009 may also be connected to first connector 1011 for coupling to cable 204. A suction device 1010 may connect on an additional external port of connector 1011 or may also connect through first connector 1011 as depicted by the optional positions for suction 1010. A water supply line 1012 is shown with the same options. The signal conversion unit 114 may be placed adjacent to connector 1011 in the CCU or other device 1004, or elsewhere inside the CCU or other device, and performs the functions described above of converting incoming optical signals from the attached scope or camera head to electrical signals for further processing and converting electrical signals generated at the CCU to optical signals for transmission to the scope or camera head. GI endoscope 1022 includes a flexible scope shaft 1021 and image sensor module 1020, which is electrically coupled to signal processor 1024 for providing image data. The image data is transmitted to optical fibers 507 (shown in FIG. 11) in cable 204 by fiber optic transmitter 1023. Typically, elements 1023 and 1024 are positioned in a scope handle while the image sensor module 1020 is positioned at the distal end of the scope shaft 1021.

Figure 12:
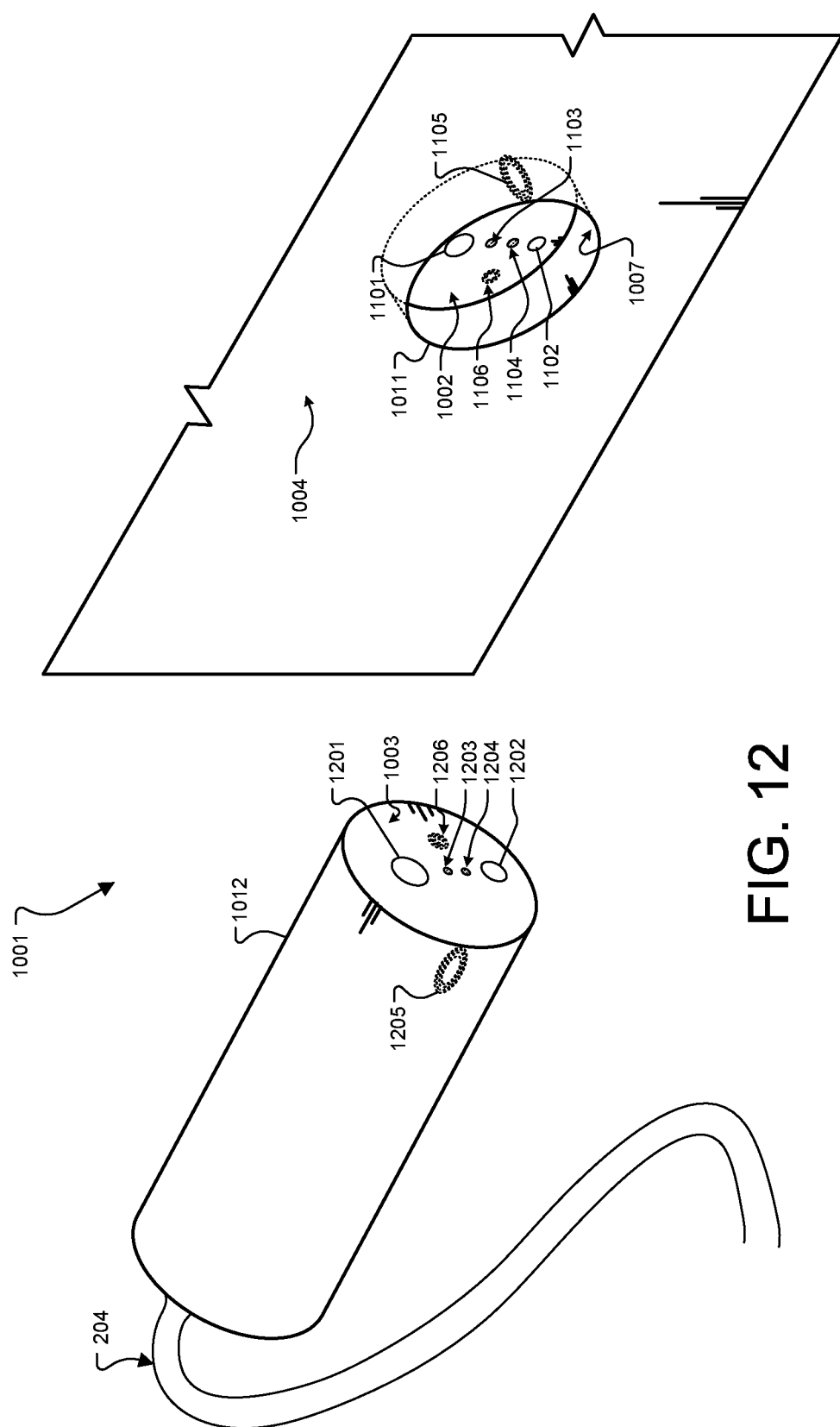
FIGS. 12-14 show perspective diagrams of different example connector embodiments.

FIGS. 12-15 show diagrams of different connector embodiments for connectors 1011 and 1012. Referring to the version of FIG. 12, depicted is an apparatus 1001 for providing a detachable data and power interface to an electrically powered medical instrument such as a GI endoscope. The apparatus includes a first connector 1011 including a first surface 1002 and a first receptacle 1007 formed at an exterior surface of CCU or other device 1004 expressing the first surface. (The receptacle may instead be an extension similar to that of FIG. 14.) To the left, a second connector 1012 is shown, the second connector 1012 is adapted to interface with the first connector 1011 in an operating position, in this case inserted into the receptacle 1007 and secured with a suitable mechanism. First connector 1011 includes a first surface 1002 and in general one or more first channels adapted to carry at least one of an optically modulated data signal, an electrical signal, illumination light, and fluid (e.g., air or liquid).

Figure 15:
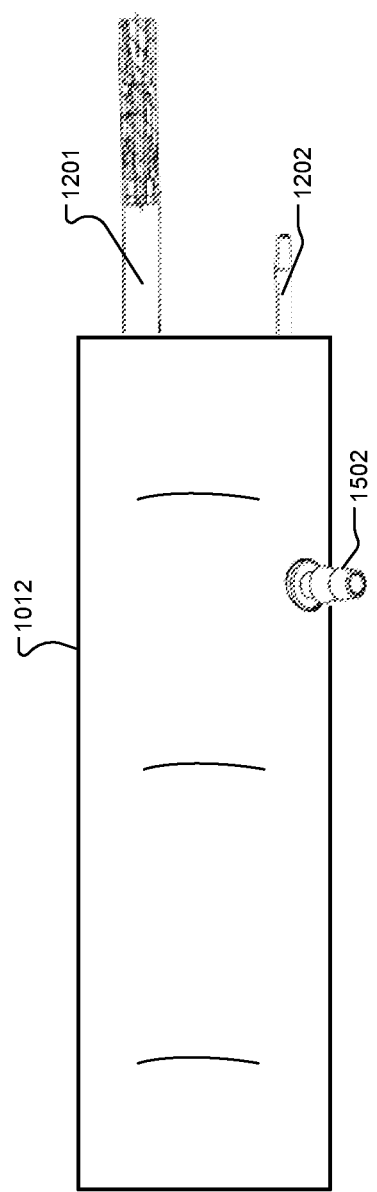
FIG. 15 is a side view diagram of an example connector.

The one or more first channels extending through first surface 1002 of the first connector 1011, each first channel terminating at a respective first channel end. Second connector 1012 generally has corresponding channels including one or more second channels adapted to carry the at least one of the optically modulated data signal, the electrical signal, the illumination light, the air, and the liquid, the one or more second channels extending through the second surface 1003. The second channels can be seen terminating at their respective channel ends along the second surface 1003, with each respective second channel being aligned for coupling across a coupling region with one of the first channels when the first connector and second connector are interfaced in the operating position. One or more of the channels may also include a projection from the surface 1002 or 1003 to form a plug for sealing and engaging the channel. For example, FIG. 15 shows a side view of a second connector 1012 showing suitable projections for channels 1201 and 1202, which in this embodiment channel 1201 carries illumination light and channel 1201 carries air supply. These projections may be made of a suitable rigid or semi rigid material or combination of materials such as plastic, metal, or ceramics, for example. The construction of such projections is known in the art and will not be further described. Care should be taken in the design to avoid placing metal structures in positions that interfere with the electro-magnetic fields created during inductive power transfer. Also shown in FIG. 15 is a suction line port 1502 to which an external suction line may be connected for supplying suction line to the instrument, such as GI endoscope, through suction line 1108 (FIG. 11). A similar port may be provided, on the opposite side of second connector 1012, for a water supply port connecting to water supply line 1106 in cable 204 (FIG. 11).

Referring again to FIG. 12, in this embodiment, modulated optical data signals are transmitted through two channels having channel ends, which in this example are lenses 1103 and 1104, present along first surface 1003 of first connector 1011, which couple signals to corresponding light channels on second connector 1012, in this example having channel ends at lenses 1203 and 1204 on second surface 1203 of second connector 1012. Light supply channel 1101 along first surface 1002 of the first connector 1011 similarly channels illumination light for the scope to light supply channel 1201 on the second connector 1012, which is coupled to the light carrier 1124 in cable 204 (FIG. 11). Air supply channel 1102 of first connector 1011 couples with air supply channel 1202 on the second connector, which is coupled to air line 1122 in cable 204. An electrical signal channel 1106 similarly couples to channel 1206, preferably by inductive coupling to provide electrical isolation, but in some cases a contact electrode may be used. This couples an electrical signal 1009 (FIG. 10) which is then carried by electrical conductor 1111 in cable 204, and may be used for operation (e.g., an electrode scalpel) or for data transfer (e.g., an electrical data signal).

Figure 14:
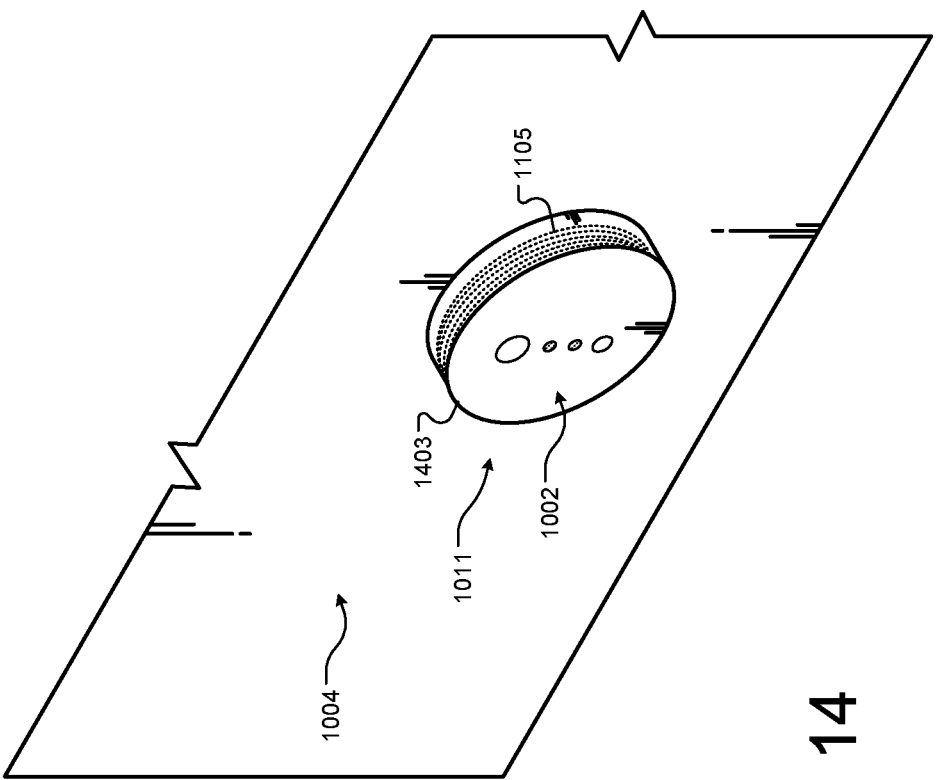
Figure 14:
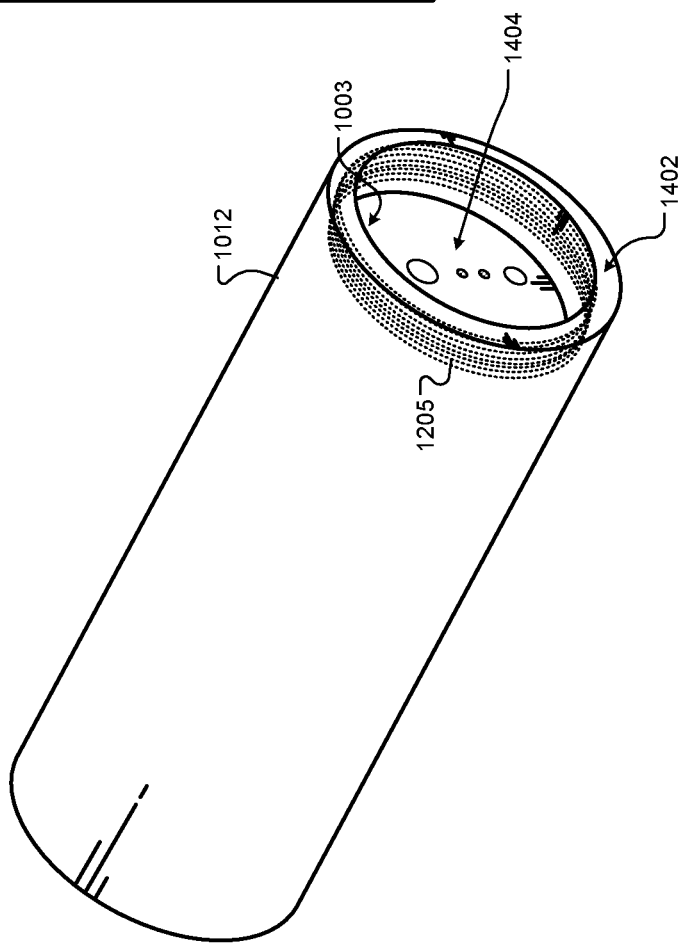

A first power transfer element 1105 is shown mounted on the first connector 1011 along at least one internal surface of the first receptacle 1007 (which may instead be an extension as shown in FIG. 14). As depicted, power transfer element 1105 in this version is an inductive coil arranged just beneath an interior surface of the first connector receptacle 1007 of CCU 1004 or other device, however this is not limiting and other suitable locations may be used as further described below. A second power transfer element 1205 is mounted on the second connector 1012 along at least one side surface, and is also depicted in this example as a coil shown in dotted lines beneath an outer surface of second connector 1012. The first power transfer element 1105 and the second power transfer element 1205 are aligned in a power transfer orientation when the first connector and second connector are interfaced in the operating position. The first power transfer element 1105 may be embodied as a first flattened inductive coil and the second power transfer element 1205 comprises a second flattened inductive coil, although other suitable power transfer elements may be used. The power transfer orientation in such case will be an orientation facilitating inductive coupling between the two inductive coils 1105 and 1205.

The one or more first channels, in this case two channels with channel ends at lenses 1103 and 1104, include first optical data conduits connected to fibers or electro-optic converters. The one or more second channels, in this case channels, again in this example shown by their channel ends at lenses 1203 and 1204, include second optical data conduits connected to respective fibers 507 in the cable 204. Each respective second optical data conduit is aligned for optical coupling across a coupling region, in this case between the two opposing optical lenses, with one of the first optical conduits when the first connector and second connector are interfaced in the operating position. The channels ending at 1203 and 1204 are coupled inside second connector 1012 to respective optical fibers 507 as shown in the cable 204 of FIG. 11. Preferably the optical channels include wavelength division multiplexing allowing multiple optical signals to be transmitted or received simultaneously. While two optical channels are shown here, more may be used, such as in the example shown in FIG. 5 where six optical channels are transmitted through six optical fibers.

In the version shown in FIG. 12, the first connector 1011 defines a receptacle 1007 and in the operating position at least a portion of the second connector 1012 is received within the receptacle 1007 defined by the first connector 1011. In this case the receptacle 1007 includes an enclosure, however other versions may not be totally enclosed with solid side walls. Further, while a first connector 1011 is shown mounted on a CCU or combi-box supply, this is not limiting and the first connector 1011 may be connected to a CCU and possibly other supply units with one or more cables. Preferably, the body of connectors 1011 and 1012, in the various embodiments herein, are constructed from a high temperature material or combination of materials such as, for example, plastic or ceramic to electrically isolate and insulate the various channels and power transfer elements. The body may also be sealed with a suitable liquid proof resin.

FIG. 11 shows a cross sectional schematic diagram of a cable structure which may be employed for cable 204 according to one or more additional embodiments in which the cable carries further channels such as an air supply line, a suction line, and a water or liquid supply line as used, for example, with gastrointestinal (GI) endoscopes. Similarly, as with the cable of FIG. 5, cable 205 has three outer layers 501, 502, and 504 that define and interior area 505 for optical fibers, electrical conductors, other channels, and reinforcing elements as desired. The elements similarly present in the cable of FIG. 5 bear the same numbering and will not be described again here. In FIG. 11, cable 204 includes a suction line 1108 for supplying suction to the medical device, which may be supplied with suction through a channel in both the first and second connectors 1011 and 1012, or through an external port on the second connector 1012. Water supply line 1126 provides water supply to the medical device, and may be similarly coupled through the connectors or through a dedicated external water port on the second connector 1012.

Figure 13:
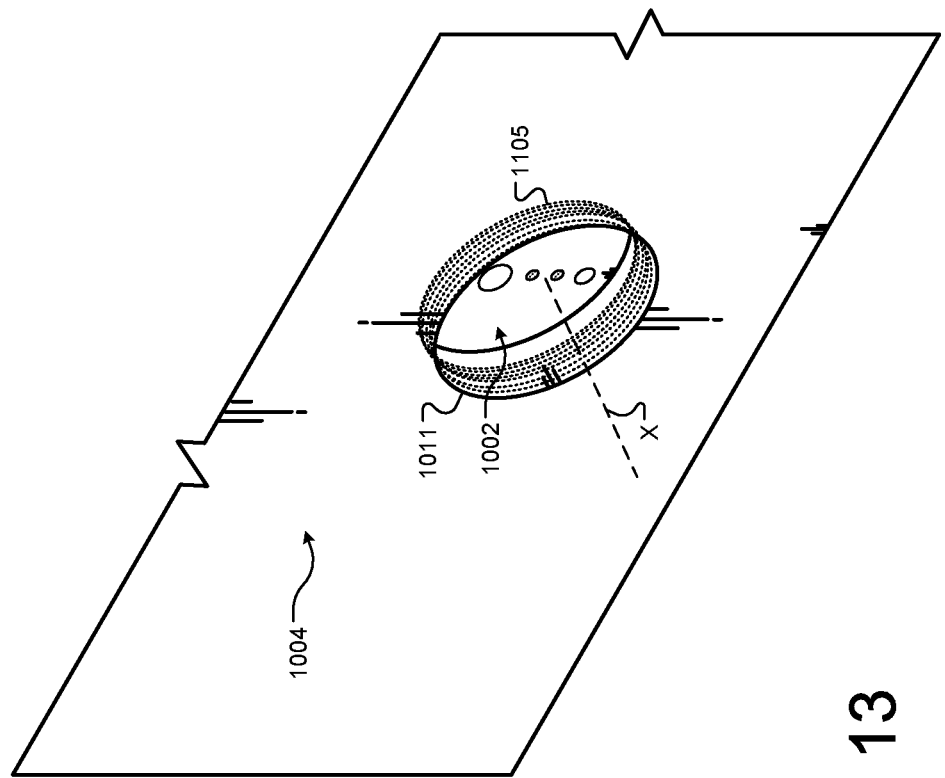
Figure 13:
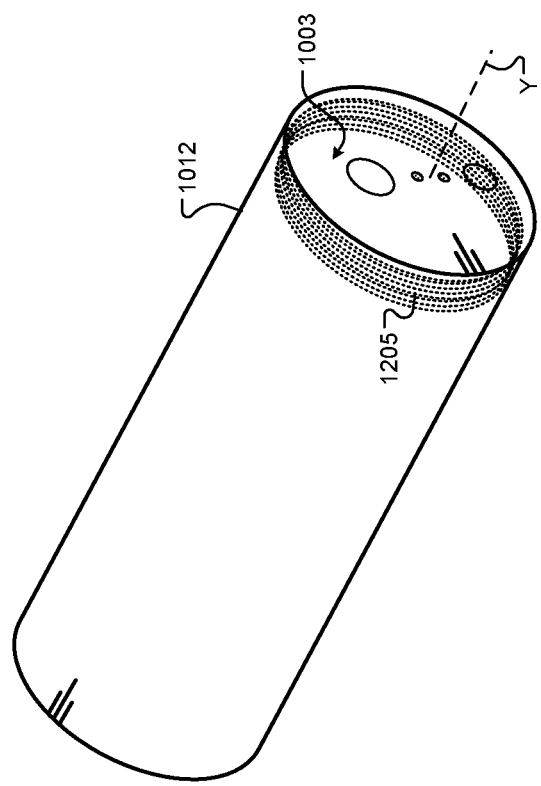

FIG. 13 is a perspective diagram showing two connectors similar to that of FIG. 12, but with the first and second power transfer elements 1105 and 1205 constructed differently. In this example version, first power transfer element 1105 is positioned within the first connector 1011 around the perimeter of the receptacle 1007 forming the first connector 1011. It may also be positioned along the first surface 1002. The first power transfer element 1105 defines a first cross-sectional shape, in this example circular, that encompasses at least one of the one or more first channels and has a first central axis X, shown by the dotted line, extending through the first surface 1002. Similarly the second power transfer element 1205 is positioned along the outer perimeter of second connector 1012, or may be positioned along the peripheral edges of surface 1003, and defines a second cross-sectional shape that encompasses at least one of the one or more second channels, with the central axis, shown by the second dotted line Y, of this shape extending through the second surface 1003. Preferably the first and second power transfer elements 1105 and 1205 are constructed as inductive coils which, in this version, are nested with second power transfer element 1205 inside first power transfer element 1105 when the connectors are placed in the operating position.

Figure 16:
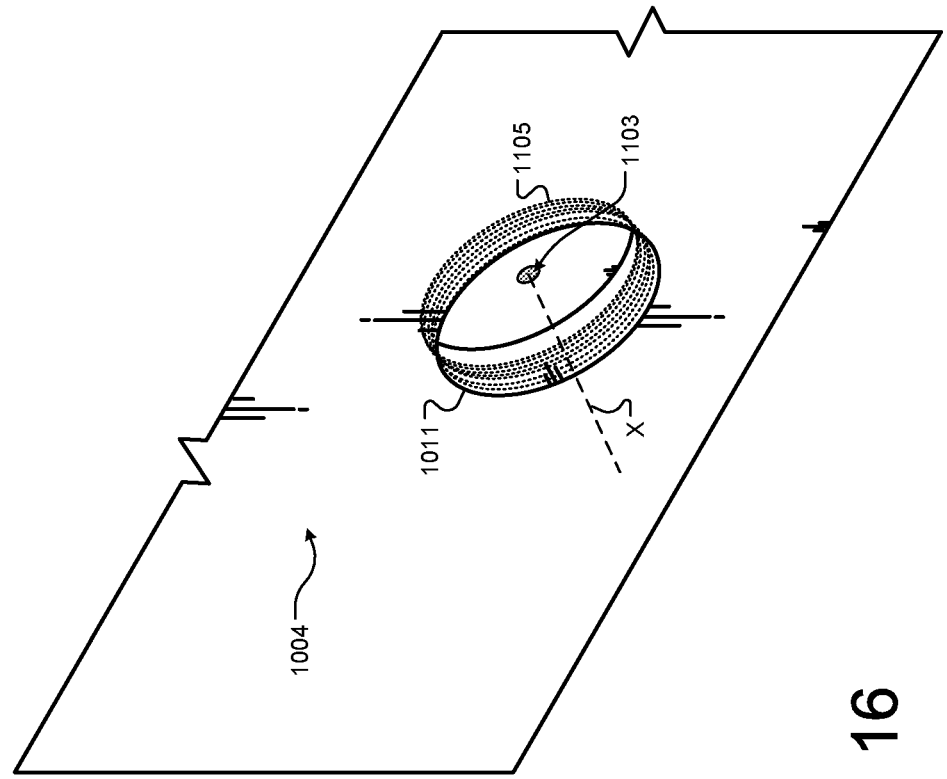
FIG. 16 shows perspective diagrams of additional example connectors.
Figure 16:
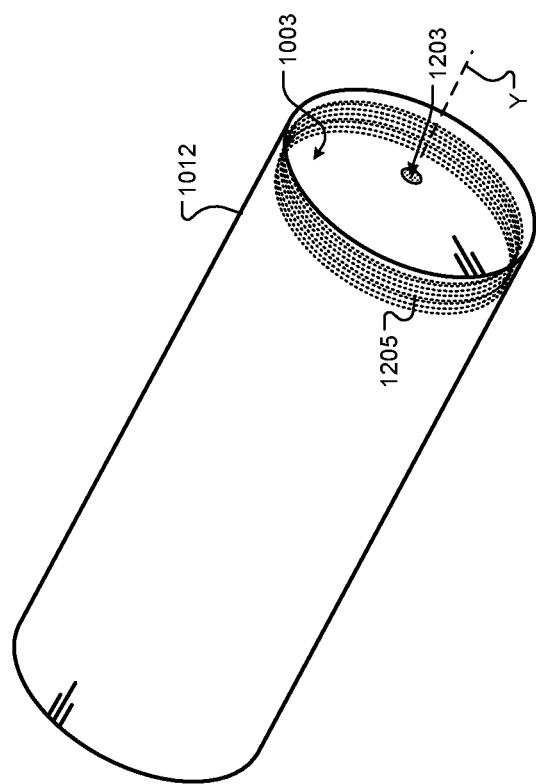

FIG. 16 shows perspective diagrams of two connectors similar to those of FIG. 13, and each having a centrally arranged optical channel, ending at lenses 1103 and 1203. In this example embodiment, the second connector 1012 may be rotated within the first connector 1011 during operation, with the position of the optical channels allowing the lenses or other optical coupling elements to maintain their optical coupling as the connector is rotated, which may be useful for endoscopic connections, for example, that often require an endoscope to be rotated during a medical procedure. As can be seen in the diagrams, the central axis X and Y of the power transfer element cross sectional shapes extends through the channels 1103 and 1203, respectively.

FIG. 14 shows perspective diagrams of two connectors according to another example embodiment. The first connector 1011 in this version is formed with a projection 1403 from the body of CCU or other device 1004, with the second connector 1012 formed with a receptacle 1404 at its end designed to fit over the projection 1403 and place second surface 1003 adjacent first surface 1002 in the operating position with the channels coupled. First power transfer element 1105 is formed along the periphery of first connector 1011 surrounding the one or more channels, and second power transfer element 1205 formed inside the walls 1402 of the second connector 1012's projection 1403. The respective power transfer elements may also be formed along the surfaces 1002 and 1003 surrounding the channels. A similar mechanical structure may be employed with the power transfer elements like those in FIG. 12, positioned along the interior of wall 1402 and the exterior of connector 1402.

Figure 17:
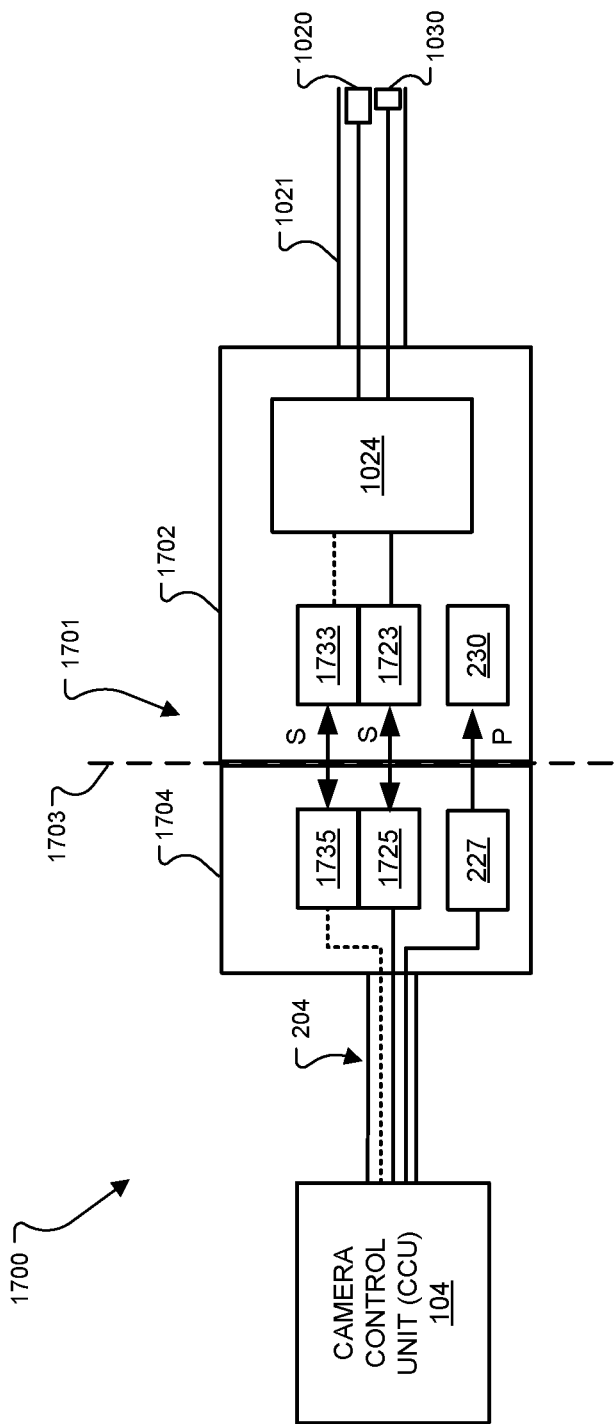
FIG. 17 is a block diagram of a medical camera system according to another embodiment of the present invention.

FIG. 17 is a block diagram of a medical camera system according to another embodiment of the present invention. The system 1700 includes a video medical scope 1701 defining an enclosed space within a distal portion 1702 and a proximal portion 1704, which are designed to couple and uncouple from each other to provide a two-part scope. Proximal portion 1704 serves as a handpiece for the scope 1701, while distal portion 1702 holds the instrument shaft. This arrangement provides several benefits such as allowing the use of disposable distal portions 1702, which may be constructed with commodity sensors and less expensive components, while allowing the scope cable 204 and proximal portion 1704 to be re-used. Another benefit is allowing a scope to be swapped out or changed easily during a procedure, such as to replace with a smaller or larger scope, or a scope with different devices integrated such as a cauterizing head or other surgical instrument. The video medical scope includes at least one image sensor for providing image data, which is typically mounted in an image sensor module 1020 positioned at the distal end tip of the scope shaft 1021. An LED 1030 or other light source may also be positioned at the distal tip for providing imaging light. The shaft 1021 can be rigid, semi-rigid, semi-flexible, flexible, with or without a channel, or with or without a flexible tip section and other configurations. Image sensor module 1020 is electrically coupled to signal processor 1024 for providing image data. A first optical modulator 1723 arranged within the distal portion and communicatively coupled preferably electrically, to the image sensor through signal processor 1024. The first optical modulator 1723 is configured to optically modulate at least the image data for transmission. A distal interface includes interface channels further described below, and is arranged within the distal portion 1024. The distal interface includes at least a first optical channel S communicatively coupled to first optical modulator 1723 and configured to transmit the optically modulated image data beyond the enclosed space and over a patient isolation barrier 1703 which is between distal portion 1702 and proximal portion 1704. Preferably the channel includes a first optical fiber connected to first optical modulator 1723, an optical lens connected to the first optical fiber and presented at or near the patient isolation barrier. The proximal interface and distal interface are adapted to releasably couple to each other with each interface lying on opposite sides of the patient isolation barrier 1703. The proximal interface includes a first optical receiver 1725 configured to receive the optically modulated image data when the first optical receiver is arranged near or on the first optical channel S. Preferably the proximal interface includes a second optical lens in the proximal portion, connected to first optical receiver 1725 via an optical fiber. Other structures may be employed for the two interfaces, such as an integrated electro-optical or opto-electrical converter coupled to a respective lens directly or through another suitable optical element besides optical fiber. While this embodiment provides one optical channel, preferably the optical channel includes wavelength division multiplexing allowing multiple optical signals to be transmitted and/or received simultaneously. That is, optical modulator 1723 and optical receiver 1725 may both be multiplexing style elements which both transmit and receive optical signals, and convert to and from electrical signals. First optical receiver 1725 may include an opto-electrical converter for transmitting the received data on cable 204, or may merely couple or relay such data down an optical fiber in cable 204. A second optical receiver 1733 may also be included at the distal portion, connected to the signal processor/controller 1024 through an opto-electric converter to relay control signaling. This connection may be two way, with control response and status day conveyed back toward the CCU 104. A similar lens pair with fiber optic channels connects receiver/transceiver 1733 to a transmitter/transceiver 1735 on the proximal portion of the medical scope 1702, and then fed back to CCU 104 through an electrical or optical channel through the cable 204. These control signaling connections are depicted as dotted lines because they may instead be included in a single channel through wavelength division multiplexing or time division multiplexing, for example.

While in this version, an optical receiver 1725 is shown in the proximal portion 1704, other versions may position the optical receiver 1725 at the opposite, proximal, end of cable 204 at the CCU. In such versions, an optical fiber or optical pathway extends from the proximal interface and is routed into cable 204 to CCU 104. There, a pair of beam expansion elements or lenses couples the optical signal off of cable 204 and into CCU 104 to an appropriate optical demodulator.

The distal and proximal interfaces, when coupled, defining a rotatable connection that allows for independent rotation, with respect to the proximal interface, of the distal interface, and preferably the entire distal portion 1702, the rotation including rotation about an axis that at least spans the distal and proximal interfaces when are coupled together as further described below. The first optical channel and first optical receiver 1725 respectively configured to maintain the optical communication channel between the first optical channel and the first optical receiver when the distal and proximal interfaces are coupled and the distal interface is rotated, with respect to the proximal interface, at least about the axis.

Distal portion 1702 includes a power transfer element 230 for contactless transfer of electrical power from power transfer element 227, which transmits power from wires or other conductors provided in cable 204. Power transfer element 227 is adapted for contactless transmission of the electrical power P when the first power transfer element 227 is placed within a near-field communication distance or power coupling distance from the first power transfer element 230. Example implementations of the two power transfer elements are further described with regard to the examples below. The electrical power may be used to operate an imaging device and related electronic components in distal portion 1702, opto-electrical and electro-optical converters associated with the distal interface, and illumination elements (not shown in the figures) associated with the image sensor module 1020. When the proximal and distal portions 1704 and 1702 are connected in the operating position, the two power transfer elements 227 and 230 are in a power transfer orientation with respect to each other, which, in this embodiment comprises an orientation in which the power transfer elements are inductively coupled. The two power transfer elements 227 and 230 are also arranged such that, when in the power transfer orientation, they continue or maintain power transfer during rotation of the distal portion 1702 with respect to the proximal portion 1704. As described with respect to other embodiments herein, power control circuitry is provided operable to supply a suitable driving signal to cause a variable current flow in first power transfer element 227 and consequent electromagnetic field around the first power transfer element. This field produced around first power transfer element 227 induces a current in second power transfer element 230. The induced current is conditioned by power receiver/conditioner circuit to provide a suitable power supply to the distal portion 1702. For example, a power receiver/conditioner circuit may comprise a suitable rectifying circuit for converting the signal induced in second power transfer element 230 to a DC voltage. This preferred arrangement of wireless power transfer between proximal and distal portions 1704 and 1702 results in complete electrical isolation between electrical circuits associated with the respective portions, achieving an electrical isolation in the power supply across patient isolation barrier 1703. This allows a cable design for cable 204, which connects to a CCU or other control module, similar to that of FIG. 5. Cable 204 includes electrical conductors for supplying power, and one or more optical fibers or optionally electrical signal channels for transmitting and receiving data along the cable.

Figure 18:
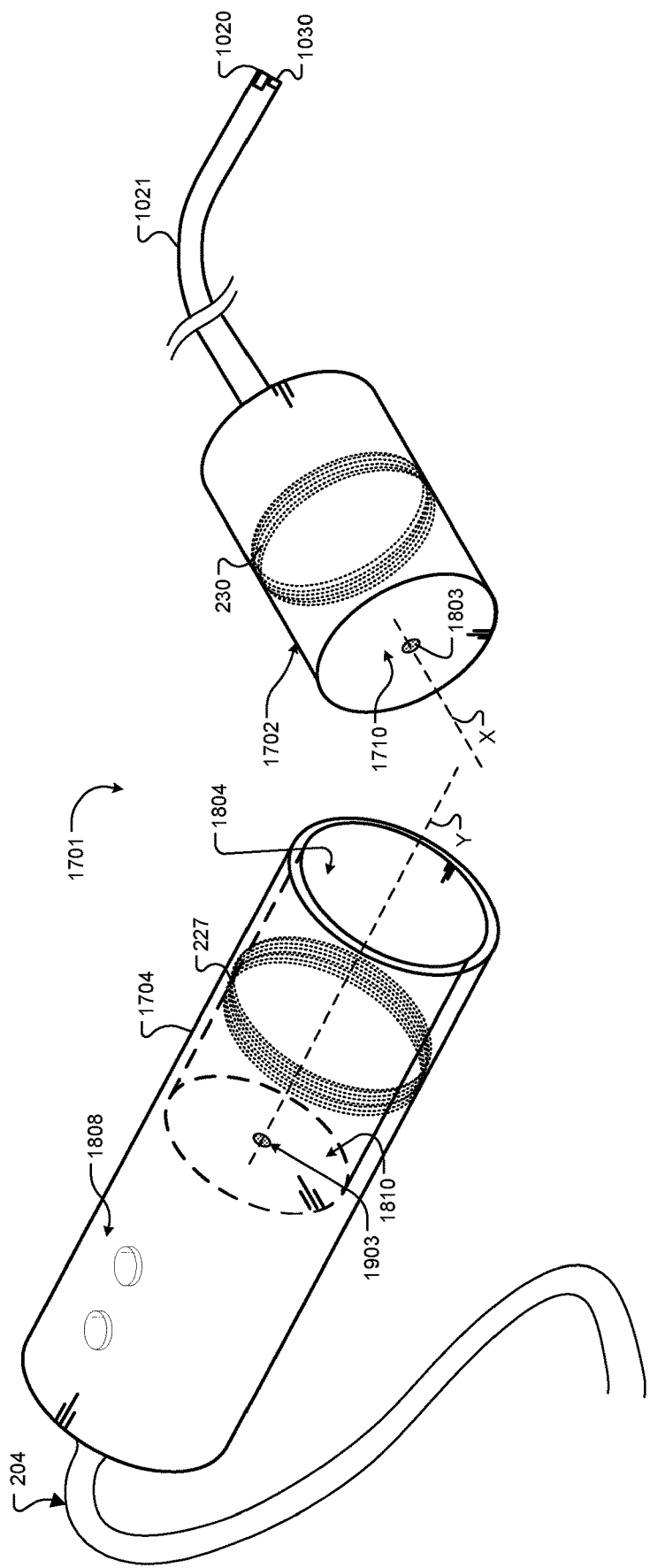
FIG. 18 is a perspective view of an example embodiment of the video medical scope of FIG. 17.

FIG. 18 is a perspective view of an example embodiment of the video medical scope 1701 shown in block diagram form in FIG. 17. The depicted video medical scope 1701 includes a distal portion 1702 is adapted to couple and release from the proximal portion 1704, allowing the two portions to be connected together in a longitudinally rigid handle portion that allows the operator to rotate distal portion 1702 while holding proximal portion 1704 as a handle. Control buttons 1808 are provided on the exterior surface of proximal portion 1704, which may be configured for various control function such as mode switching, on/off or zooming, for example. Control buttons may instead be placed on distal portion 1702. Button signals may be transmitted to the distal portion 1702 for use by the signal processor and controller 1024 is controlling the camera and imaging light electronics. This may be done by modulating the signals onto the inductive power transfer signal transmitted from power transfer element 227 with a suitable known modulating circuit, and demodulating the signal from the power signal receives by power transfer element 230 with a suitable known demodulating circuit to feed the button signal to controller 1024. The button signal may also be routed down the cable electrically and introduced into control signaling which is transmitted optically back up the cable and across the patient isolation barrier optically. In this version, proximal portion 1704 presents a cylindrical cavity 1804 into which the distal portion 1702 is inserted like a plug. This is not limiting, and other versions may have other machinal designs suitable for providing the desired coupling, such as, for example a reversal of the depicted shapes in which distal portion 1702 has a cylindrical cavity and proximal portion 1704 fits inside the cavity. As another example, design may include a post on proximal portion 1704 onto which the distal portion 1702 may fit, or a two-sided clamp design for proximal portion 1704, for example. A suitable latch, pin and groove, or other locking mechanism may be used to hold the coupled portions together and still allow rotation while coupled. In the coupled position, distal portion 1702 is inserted into cavity 1804, placing its proximal face 1710 against distal face 1810 of proximal portion 1704, the inner or back wall of the cylindrical cavity.

Referring to FIGS. 17 and 18, the distal portion 1702 has a longitudinal central axis X. A lens 1803 or other optical expansion element, which is the channel end for the first optical channel connected to first optical modulator 1723, is centered along the central axis X. A similar lens or optical expansion element 1903, which is the channel end for the optical channel to receiver 1725 in the proximal portion 1704, is positioned along face 1810 centered along the central axis Y of proximal portion 1804. In the coupled position, lenses 1803 and 1903 face each other for transmitting optical signals between the two. They may contact or a gap may be present as discussed above with regard to the use of optical lenses for fiber optic transmission. Because the lenses 1803 and 1903 are centrally located about the axis of rotation of the medical scope 1701 in the coupled position, rotation of the distal portion 1702 relative to the proximal portion does not cause loss of connectivity for optically transmitting data through the optical from optical modulator 1723 to receiver/demodulator 1725.

In FIG. 18, power transfer element 230 of distal portion 1702 is seen as a helical induction coil embedded near the outer surface distal portion 1702, for wirelessly receiving electrical power over the patient isolation barrier from power transfer element 227, which, in this embodiment, embedded or presented along the interior wall of cylindrical cavity 1804. The two power transfer elements 227 and 230 are also arranged such that, when in the power transfer orientation element 230 is nested inside element 227, and they continue or maintain power transfer during rotation of the distal portion 1702 with respect to the proximal portion 1704. While in this versions, nested inductive coils are used, other versions may employ a pair of flat coils presented along, or embedded along, faces 1710 and 1810. In such case, the coils would circle the central axis of rotation and so maintain a power transfer orientation when rotated distal portion 1702 is rotated with respect to proximal portion 1704 in the coupled position.

Figure 19:
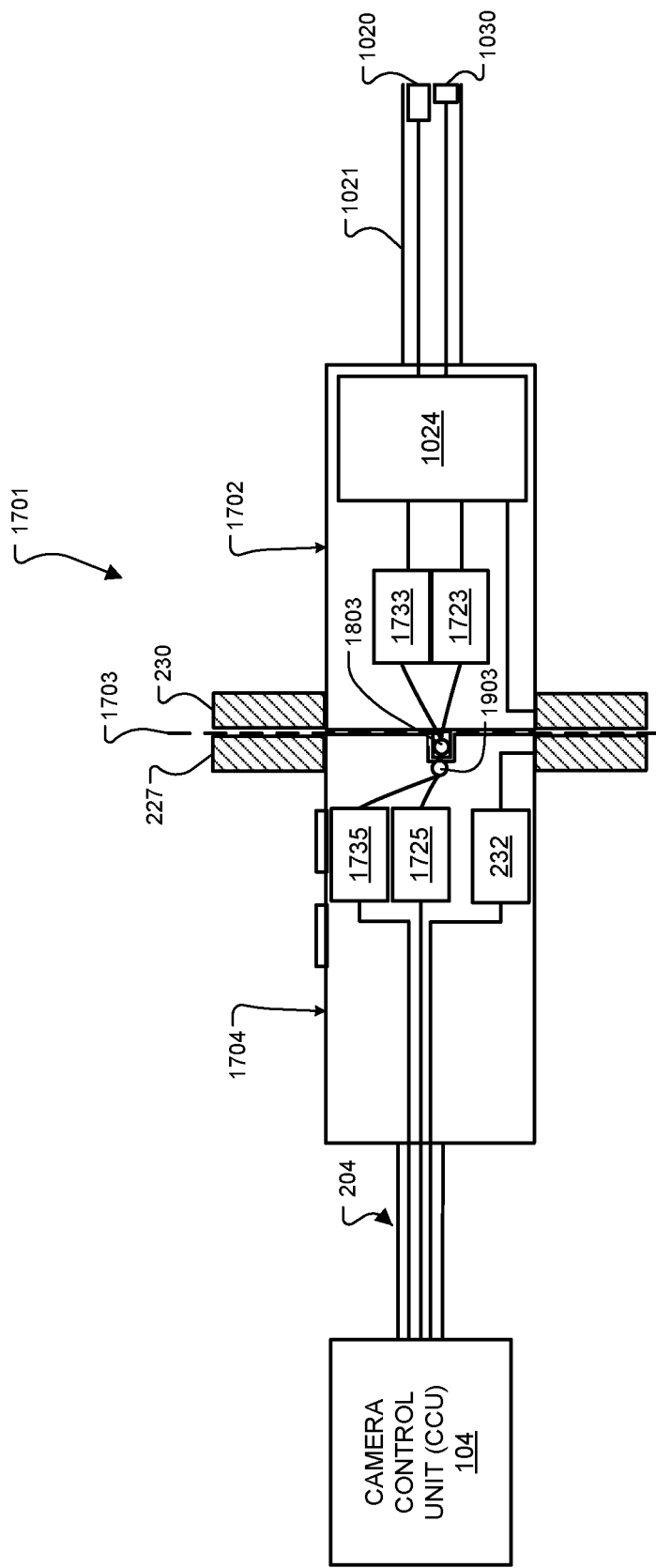
FIG. 19 is a cross-section schematic block diagram of another example video medical scope for use in a system herein.
Figure 20:
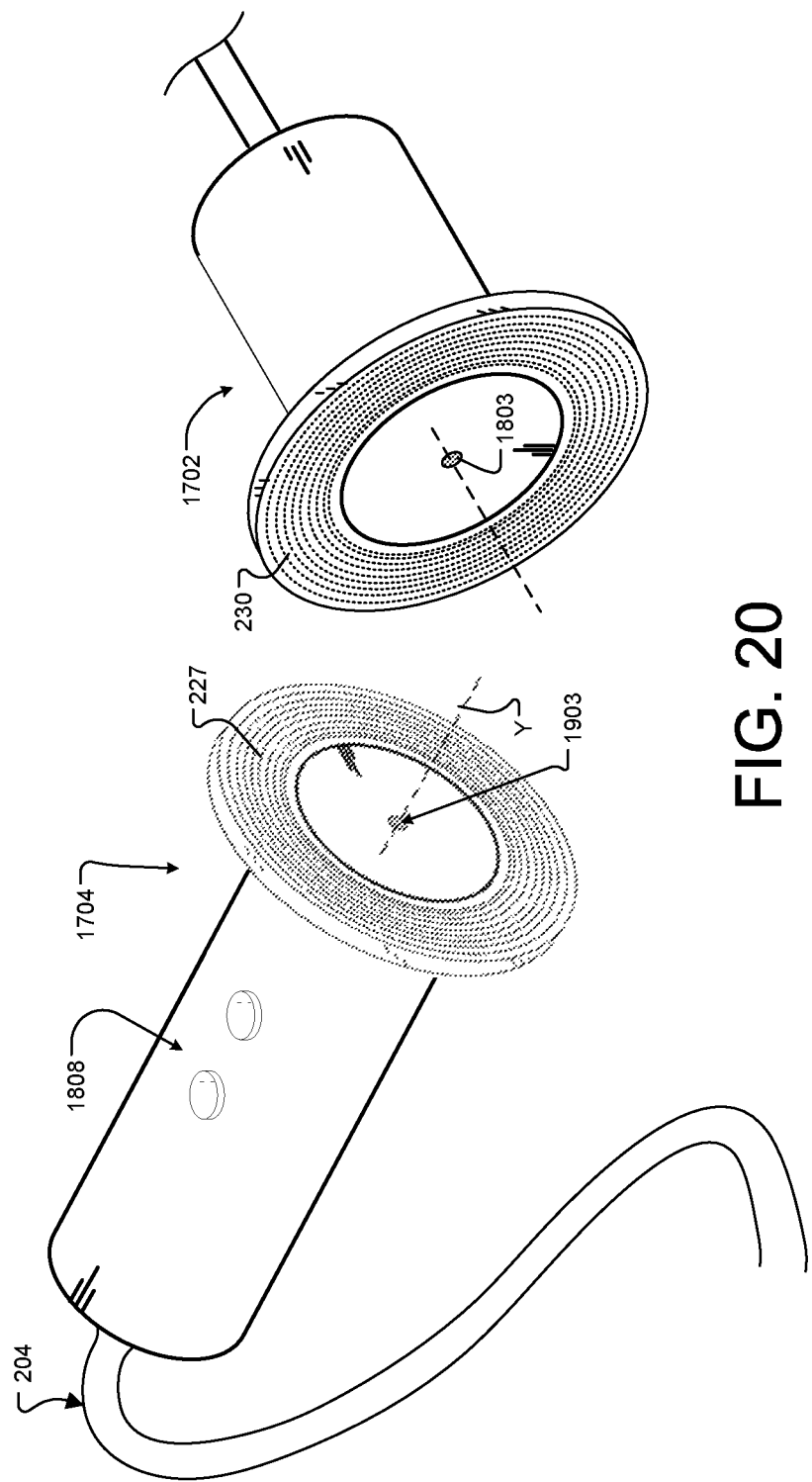
FIG. 20 is perspective view of the video medical scope of FIG. 19.

FIG. 19 is a cross-section schematic block diagram of another example video medical scope for use in a system herein. FIG. 20 is perspective view of the video medical scope of FIG. 19. Referring to both figures, the depicted scope is somewhat similar to that of FIG. 18, including two parts, distal portion 1702 and proximal portion 1704, which couple and uncouple and allow the communication link to be maintained when rotating distal portion 1702 with respect to proximal portion 1704 in the coupled state. In this version, the two power transfer elements 227 and 230 are also positioned as opposing flat inductive coils surrounding opposing faces of the elements 1702 and 1704. The coils are embedded within a ring structure extending from each portion along or near the end faces at which the distal and proximal portions couple. In the coupled configuration, as shown in FIG. 19, power transfer elements 227 and 230 are in a power transfer orientation with the inductive coils arranged adjacent each other. In this version, a single optical channel carries the image data from the scope to the CCU 104, and carries control data to the scope.

In the distal portion 1702, an expansion lens 1803 or other expanding beam optical component is shown presented in an extension along the proximal side of distal portion 1702. The expansion lens 1803, as discussed above with respect to the other embodiments herein, serves to expand and collimate the optical signal supplied over fiber optics from optical modulator 1723 and feed it to opposing lens 1903. Expansion lens 1803 also serves receive an expanded optical signal from lens 1903 and feed it to the fiber optic connection to fiber optic demodulator/receiver 1733. A similar pair of optical transmitter or modulator 1725 and optical receiver or demodulator 1735 are present on the proximal portion connected by fiber optics or other suitable optical channel to expansion lens 1903. A recess is provided in the face of proximal portion 1704 in this version, into which the extension holding lens 1903 is fits in the coupled position as depicted. This is not limiting and the recess may be on the distal portion 1702, or the lenses may be presented at the surface without a recess or extension.

Note that while fiber optic transmission using optical signals is described in some embodiments for providing communication across the patient isolation barrier, this is not limiting and other embodiments may use opto-electric components without fiber optic elements.

Figure 22:
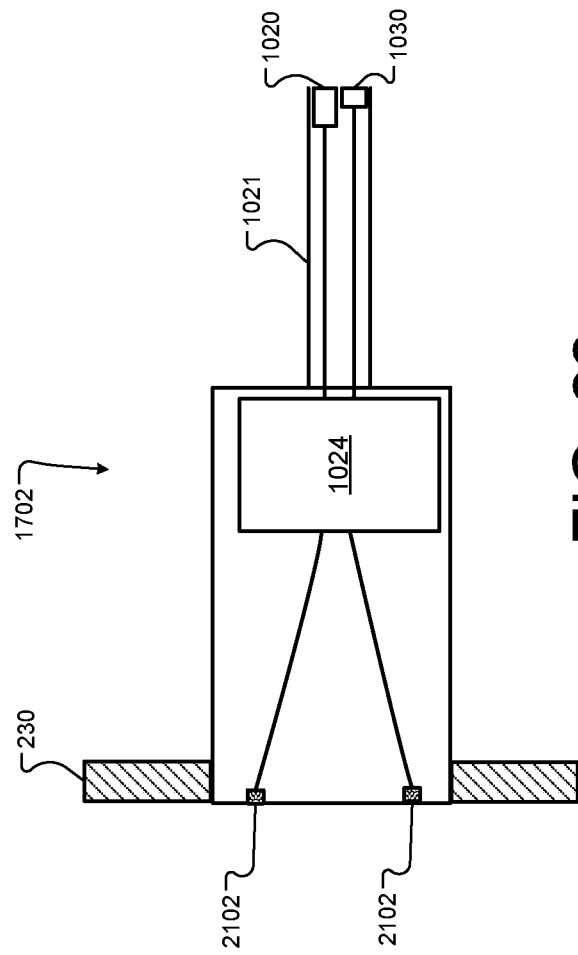
FIG. 22 is a side view block diagram of the element of FIG. 21.
Figure 21:
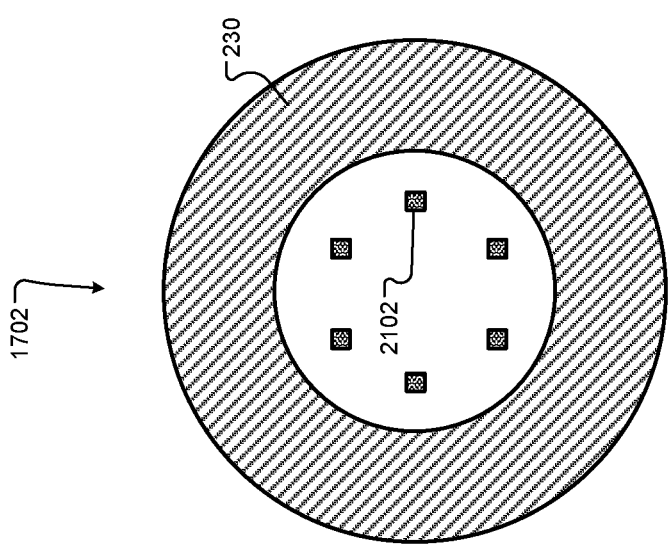
FIG. 21 is an end-on diagram view of a distal portion of another example embodiment of a two-part scope.

For example, FIGS. 21-22 show a version in which several LED emitter/receiver pairs, which may include standard LEDs or laser diodes, are employed for communication. FIG. 21 is an end-on diagram view of a distal portion 1702 of another example embodiment of a two-part scope. FIG. 22 is a side view block diagram of the same element 1702. In this embodiment, a power transfer element 230 receives power from a proximal portion similarly to that of FIG. 21. Data communication is achieved by several LED emitter/detector pairs 2102, which are electrically connected to signal processor 1024 for transmitting the image data to the proximal portion, and for receiving control data from the proximal portion. Each element 2102 may contain both an LED emitter and detector for 2-way communication according to a suitable short range light communication standard such as IRDA. In some versions, one or more of the elements 2102 may be only an LED emitter, for communicating with a matching light detector on the proximal portion. However, the use of emitter/detector pairs allows the coupled distal portion 1702 to be rotated with respect to the proximal portion 1704 and maintain the communication link. The LED emitter/detector pairs 2102 are arranged at similar radial positions around the proximal face of distal portion 2702, allowing communication links to be maintained after rotation by receiving at a first receiver 2102 before rotation, and then receiving at a second, different receiver 2102 after rotation. In this version there are six LED emitter/detector pairs presented at the proximal face of distal portion 1702.

Figure 23:
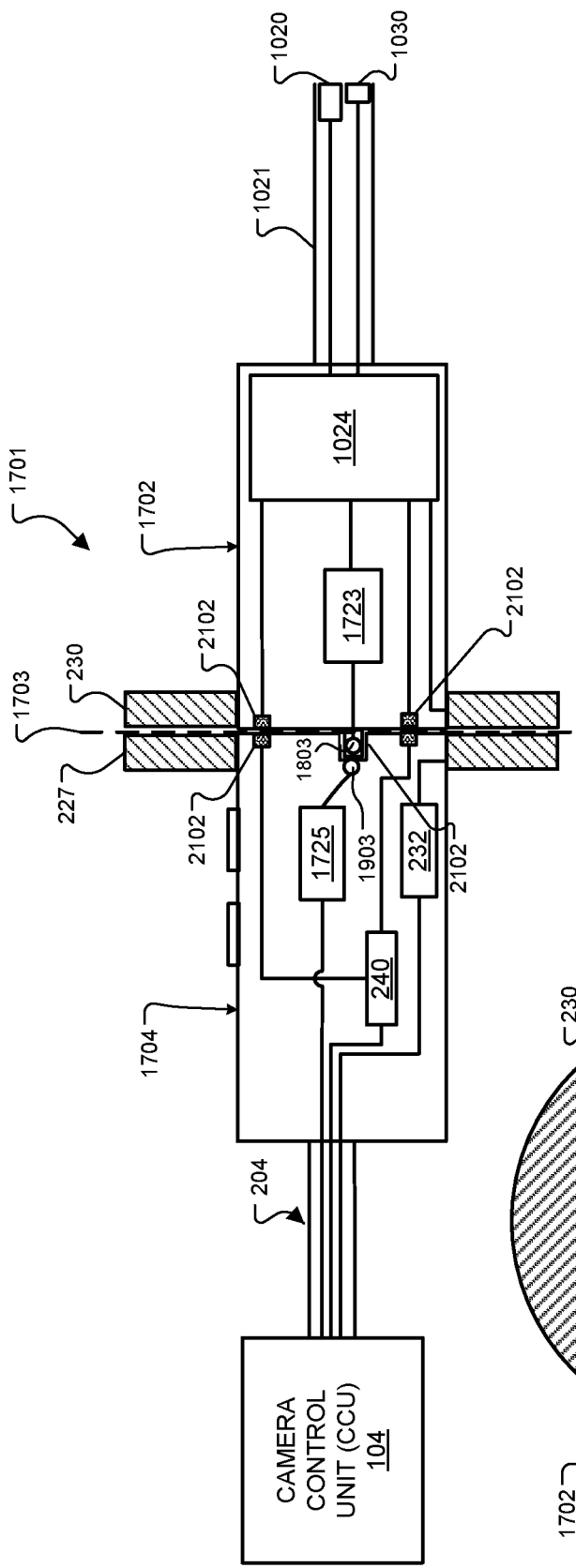
FIG. 23 is a side view block diagram of a medical camera system according to another embodiment.
Figure 24:
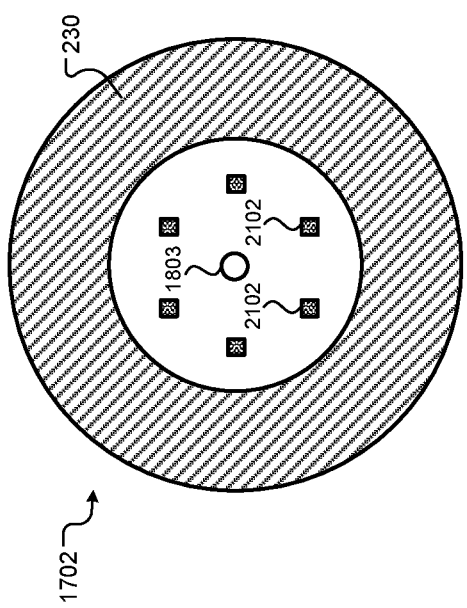
FIG. 24 is an end-on diagram view of a distal portion of the medical camera system of FIG. 23.

FIG. 23 is a side view block diagram of a medical camera system 1701 according to another embodiment. FIG. 24 is an end-on diagram view of a distal portion 1702 of the medical camera system of FIG. 23. This embodiment is a medical scope having detachable proximal and distal portions 1704 and 1702 with power transfer elements 227, 230 and generally functions as described with respect to the prior embodiments, including allowing rotation of distal portion 1702 with respect to proximal portion 1704 while maintaining the communications links when the distal portion 1702 is rotated with respect to the proximal portion 1704. In this version, there are two different types of communication link for transferring data across the patient isolation barrier 1703 between the proximal and distal portions. A first higher bandwidth link includes a lens 1803 or other optical expansion element, which is the channel end for the first optical channel connected to first optical modulator 1723, is centered along the central axis X. A similar lens or optical expansion element 1903, which is the channel end for the optical channel to receiver 1725 in the proximal portion 1704, is positioned recessed, or flush, along face 1810 centered along the central axis Y of proximal portion 1804. In the coupled position, lenses 1803 and 1903 face each other for transmitting optical signals between the two for carrying image data from the camera at relatively high bandwidth. In this version, control data is carried by a second communications means, typically a much lower-bandwidth system than the optical signaling, including several LED emitter/detector pairs 2102. The emitter/detector pairs may be one-directional (i.e. emitters only on the proximal portion 1704 and detectors only on distal portion 1702) or two-way in which both proximal and distal portions include emitters and detectors at each designated element 2102. The emitter detector pair may be driven with communications signals by a local communications controller 240 positioned in proximal portion 1704 communicatively linked to CCU 104 as shown, or may be driven directly through electrical connections passed through cable 204.

Figure 25:
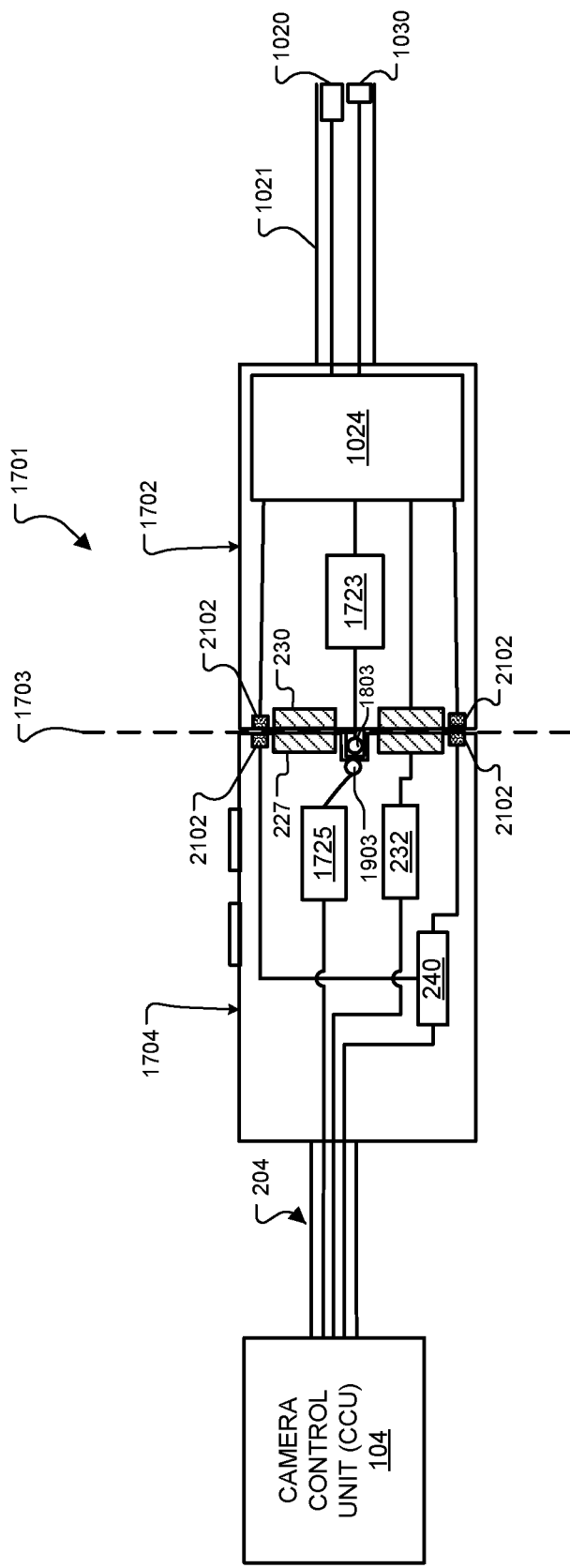
FIG. 25 is a side view block diagram of a medical camera system according to another embodiment.
Figure 26:
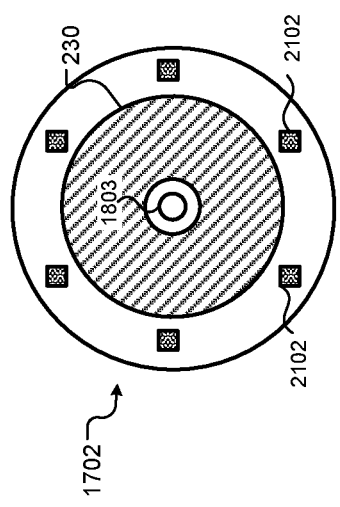
FIG. 26 is an end-on diagram view of a distal portion of the medical camera system of FIG. 25.

FIG. 25 is a side view block diagram of a medical camera system 1701 according to another embodiment. FIG. 26 is an end-on diagram view of a distal portion 1702 of the medical camera system of FIG. 25. This embodiment is another example a medical scope having detachable proximal and distal portions 1704 and 1702 which, when coupled or attached to each other, allow rotation of distal portion 1702 with respect to proximal portion 1704. The power transfer elements 227, 230 are positioned embedded at the opposing end faces of proximal portion 1704 and distal portion 1702. As can be seen in FIG. 25, the power transfer elements are, in this version, radially inside the arrangement of LED emitter/detectors 2102, and surrounding the higher bandwidth optical connection provided by optical expansion elements 1803 and 1903. The emitter/detector pairs are presented at the opposing faces, along a circle radially outside the power transfer elements 227 and 230. While as shown there are two different types of communication link for transferring data across the patient isolation barrier 1703 similarly to the embodiment of FIG. 23, this arrangement of power transfer elements may also be employed with the optical communication scheme used in the embodiment of FIG. 19 in which two-way communications are used with WDMA or TDMA multiplexing on the optical link. Similarly, this arrangement power transfer elements may also be employed with the communications scheme of the embodiment of FIG. 22, in which LED emitter detector pairs 2102 are used in parallel to achieve higher bandwidth communications without a fiber-optic link for transferring image data from distal portion 1702. Further, the design of FIG. 25 may be employed with a mechanical design for the body of the distal and proximal portions 1702 and 1704 such as that of FIG. 18, with a receiving cavity formed in either the distal or proximal portion to receive the opposing portion.

The various components of an interface according to the present invention may be formed from any suitable material or combination of materials. The materials should be selected for compatibility with environment in which the interface is to be used or to which the interface may be subjected. For example, connectors may be formed from suitable thermoplastics. With regard to cable 204 shown in FIG. 5, cover 501 may comprise reinforced silicone rubber, and EMF shielding may comprise a suitable fine gauge conductive mesh. Filler/reinforcing strands 508 and 515 may be formed from any suitable material which is compatible with the other elements in cable 204 and provides the desired strength characteristics.

Figure 27:
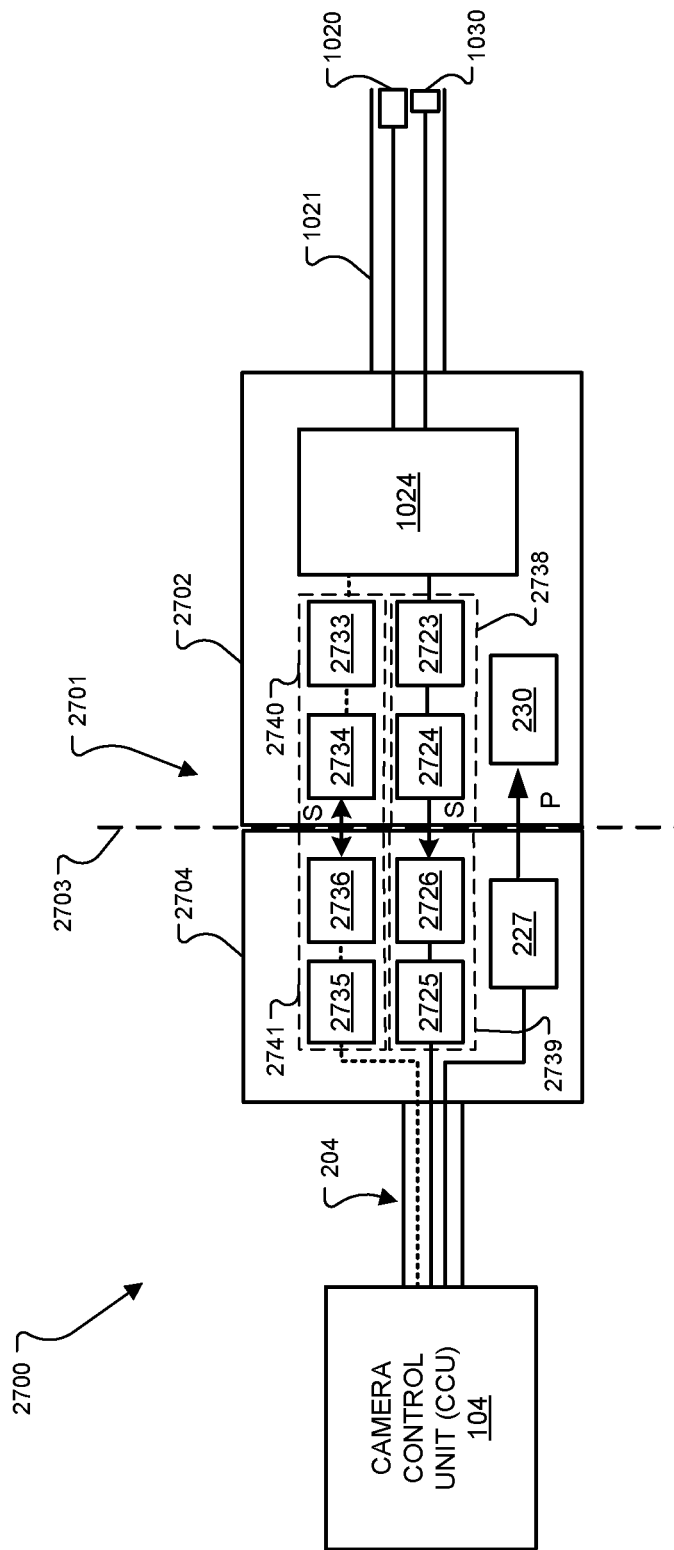
FIG. 27 is a block diagram of a medical camera system according to another embodiment.

FIG. 27 is a block diagram of a medical camera system according to another embodiment of the present invention using radio frequency (RF) transmission to send data across the patient isolation barrier 2703. The depicted system 2700 includes a video medical scope 2701 defining an enclosed space within a distal portion 2702 and a proximal portion 2704, which are designed to couple and uncouple from each other to provide a two-part scope. Similarly to the previous embodiment, proximal portion 2704 serves as a handpiece for the scope 2701, while distal portion 2702 holds the instrument shaft, providing all the advantages of interchangeability, reconfiguration, and disposability discussed above.

Distal portion 2702 includes a power transfer element 230 for wirelessly receiving electrical power over the patient isolation barrier from power transfer element 227, which transmits power from wires or other conductors provided in cable 204. Power transfer element 227 is adapted for wirelessly transmitting the electrical power P when the first power transfer element 227 is placed within a near-field communication distance or power coupling distance from the first power transfer element 230. Design considerations for the two power transfer elements are discussed above and will not be repeated here. The electrical power may be used to operate an imaging device and related electronic components in distal portion 2702. When the proximal and distal portions 2704 and 2702 are connected in the operating position, the two power transfer elements 227 and 230 are in a power transfer orientation with respect to each other, which, in this embodiment comprises an orientation in which the power transfer elements are inductively coupled. Preferably, the two power transfer elements 227 and 230 are also arranged such that, when in the power transfer orientation, they continue or maintain power transfer during rotation of the distal portion 2702 with respect to the proximal portion 2704.

The video medical scope 2701 includes at least one image sensor for providing image data, which is typically mounted in an image sensor module 1020 positioned at the distal end tip of the scope shaft 1021. An LED 1030 or other light source may also be positioned at the distal tip for providing imaging light. In other examples, the light source may be provided by an external light source coupled to the scope 2701 with a light cable for transmission via one more light guides within the shaft 1021. The shaft 1021 can be rigid, semi-rigid, semi-flexible, flexible, with or without a channel, or with or without a flexible tip section and other configurations. Image sensor module 1020 is electrically coupled to signal processor 1024 for providing image data. A first RF transmitter or transceiver modulator 2723 arranged within the distal portion and communicatively coupled preferably electrically, to the image sensor through signal processor 1024. The first RF transmitter or transceiver 2723 includes at least an RF modulator and may include an RF amplifier. The output of RF transmitter or transceiver 2723 is connected to a first RF antenna 2724. RF antenna 2724 is part of a distal interface including interface channels further described below, and is arranged within the distal portion 1024.

The proximal interface includes a first RF receiver or transceiver 2725 having a second antenna 2726 and configured to receive the image data when the two portions 2702 and 2704 are coupled. A first RF channel, shown by the lower depicted signal path S, is formed by RF transmitter or transceiver 2723 configured to transmit the RF modulated image data beyond the enclosed space and over a patient isolation barrier 2703 (which is between distal portion 2702 and proximal portion 2704) to second RF antennal 2726 which is coupled to RF receiver or transceiver 2725. The proximal interface and distal interface are adapted to releasably couple to each other with each interface lying on opposite sides of the patient isolation barrier 2703.

A second RF channel may be used in some versions for transmitting control data, shown by the upper depicted RF signal path S formed by a transmitter or transceiver 2735 coupled to antenna 2736 in the proximal portion 2704, and a corresponding antenna 2734 and receiver or transceiver 2733 in the distal portion 2702. Some versions may share antennas 2724 and 2726 to transmit and receive the second RF channel by modulating on different frequencies and mixing both channels with an appropriate RF combiner and splitter connected to each antenna. Or, if transceivers are used for elements 2725 and 2723, both control and image data may be sent over the first RF channel.

In some embodiments, video medical scope 2701 may further include a first faraday cage structure 2738 positioned surrounding the first RF antenna 2724 in all directions excepting the proximal direction, and a second faraday cage structure 2739 positioned surrounding the second RF antenna 2726 in all directions excepting the distal direction. The faraday cage structures are preferably formed of a metal such as copper, or another suitable conductor, and surround their respective antennas on all sides, with an opening or open side facing the opposing faces of distal and proximal portions 2702 and 2704. Such an arrangement serves to reduce or eliminate RF emissions outside of video medical scope 2701 by forming a nearly complete faraday enclosure or faraday cage enclosing the first transmission channel when the distal and proximal portions are joined. To preserve the patient isolation barrier's electrical isolation characteristics, the faraday cage structures are preferably built extending inside the respective housings of distal portion 2702 and proximal portion 2704 as closely as possible to the outer face of the housing while still including an insulative layer over the edges of the faraday cage structures to prevent an electrically conductive path forming between the two faraday cage structures. If two RF channels are used with two separate antennas as shown, faraday cage structures 2738 and 2739 may also enclose the antennas 2734 and 2736, respectively to allow all RF emissions to pass within a single faraday enclosure, or a separate faraday enclosure may be formed with an additional faraday cage structure 2740 and 2741 surrounding antennas 2734 and 2736 respectively. As shown, the faraday cage structures may enclose the receiver/transmitter circuitry including the electrical coupling to the antennas, or they may enclose only the antennas with a suitable aperture allowing the modulated signal to be coupled into the faraday cage structure.

Figure 28:
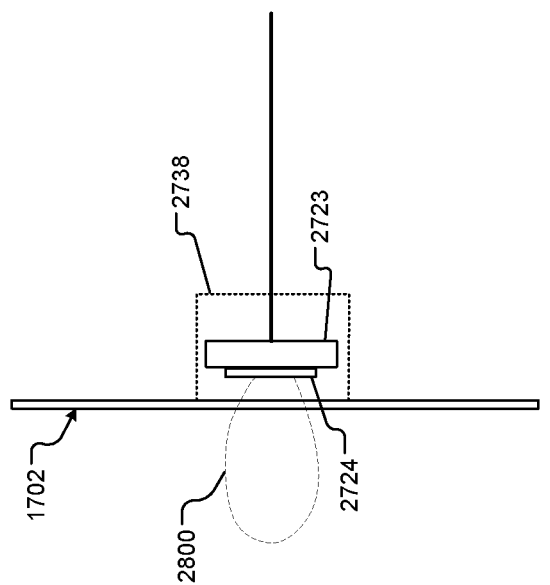
FIG. 28 shows a partial cross-sectional view of the proximal interface of the distal portion according to an example embodiment.

FIG. 28 shows a partial cross-sectional view of the proximal interface of the distal portion 1702 according to an example embodiment. In this version, the first RF antenna 2724 comprises a short range low power RF antenna. Depicted is an example antenna radiation pattern 2800 showing the directionality of the antenna 2724. The second antenna on the proximal side will have a similar radiation pattern facing the first antenna, providing an arrangement where the first RF antenna 2724 is a directional antenna having a directional emission pattern directed toward the second antenna 2726, and the second RF antenna is a directional antenna having a directional emission pattern directed toward the first RF antenna. A faraday cage structure 2738 may be used, or if the RF radiation is sufficiently low the structure may be left out. Antenna 2724 may be centrally located along an axis of rotation, allowing the proximal portion and the distal portion rotate with respect to each other without losing RF reception.

Figure 29:
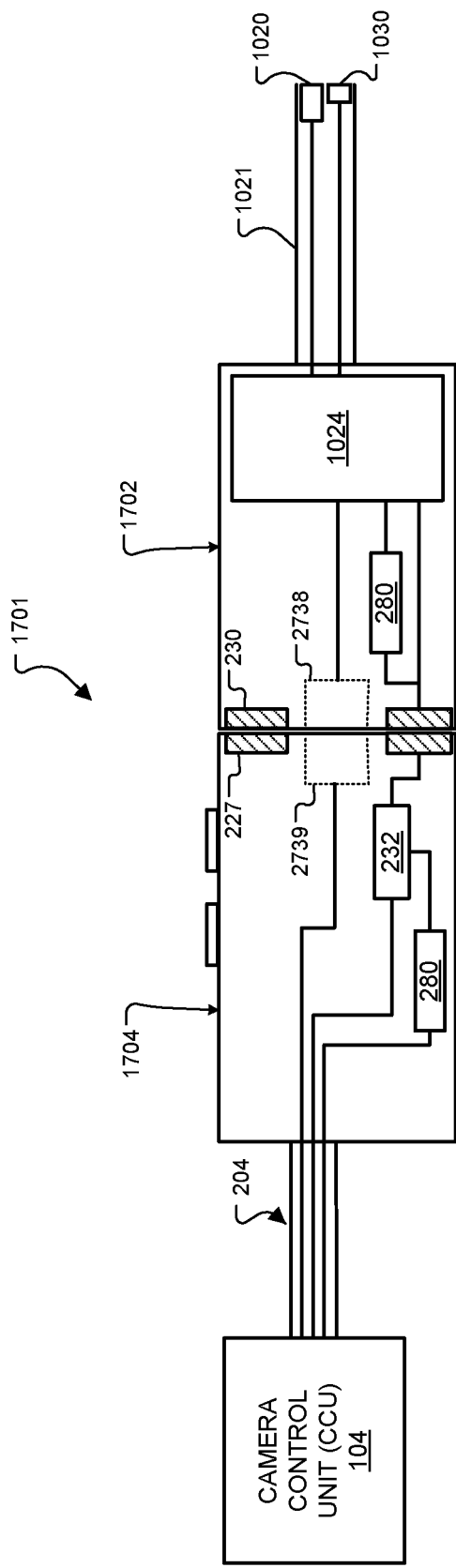
FIG. 29 is a cross-sectional diagram of an embodiment which modulates control data onto a power transfer field.
Figure 30:
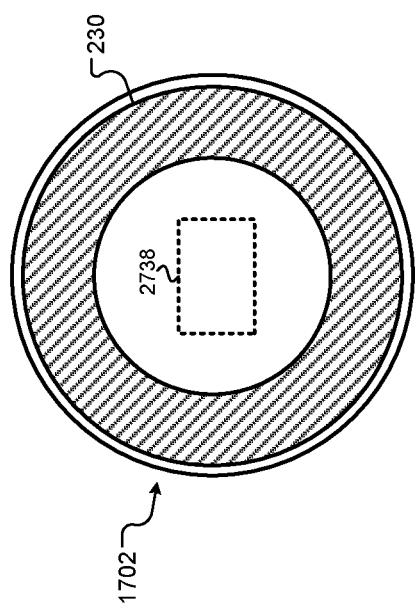
FIG. 30 shows an end-on diagram of distal portion of the same embodiment.

As discussed above with regard to other embodiments, one-way or two-way transmission of the control data may instead be accomplished by modulating control data onto a power transfer electro-magnetic field. FIG. 29 is a cross-sectional diagram of such an embodiment, with FIG. 30 showing an end-on diagram of distal portion 1702 of the same embodiment. As shown, the power transfer elements 227 and 230 include circular coils positioned underneath the opposing surfaces of the proximal and distal portions 1702 and 1704. The surface is constructed of insulative material to maintain the electrical isolation barrier. A pair of data modulator/demodulators 280 are electrically coupled to the power transfer elements, with the data modulator/demodulator 280 of the proximal portion connected through cable 204 to the CCU to receive control data. The data modulator/demodulator 280 of the distal portion receives the control data coupled through the coils of power transfer elements 227 and 230, and passes it to signal processor 1024 to control the settings. Confirmation and status information may be sent as control data from signal processor 1024 using the same techniques in reverse. This arrangement requires only one RF channel with transmit and receive antennas as discussed above shielded inside faraday cage structures 2738 and 2739. It also allows the use of a transmit-only RF scheme for the image data, while the lower-bandwidth control data is passed over the power link while still providing an isolation barrier between the proximal and distal portions 1704 and 1702. The faraday cage structures 2738 and 2739 may enclose additional electrical features within the distal portion 1702 and the proximal portion 1704.

Figure 31:
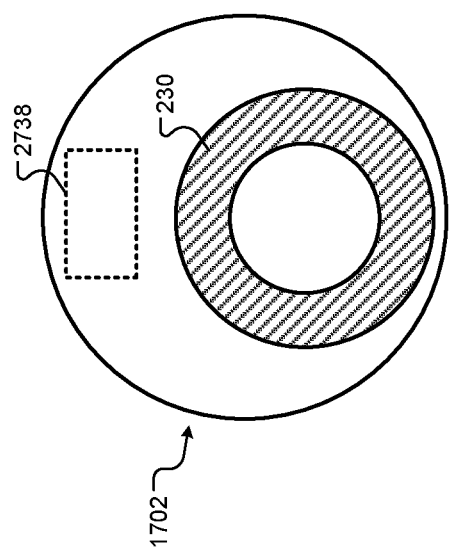
FIG. 31 shows an end-on view of another example distal portion having the faraday cage structure positioned outside of the coils of power transfer element.

FIG. 31 shows an end-on view of another example distal portion 1702, similar to that of FIG. 30, but having the faraday cage structure positioned outside of the coils of power transfer element 230 to allow for more efficient coupling of power. The proximal portion 1704 of this design has similar elements in opposing positions.

Referring to embodiments that employ RF data transmission, the particular modulation format, bandwidth, and power transmission level used to transmit the image data and control data may vary. If two RF channels are used, the control channel (between 2733 and 2735) may have a much lower bandwidth because of the much lower data bit rates required for control data versus the image data transmission. For the image data (first RF channel), a two-way wireless connection such as a PAN (personal area network) standard or a wireless networking standard may be used allowing control data to be passed. Or a one-way connection such a one-way wireless video transmission standard may be used. The power level should be reduced from typical wireless network or video transmission applications because of the extreme proximity of antennas 2726 and 2724 to each other. Preferably a known standard is used with the transmit power adjusted, the standard having a bandwidth sufficient for standard definition resolution, HD resolution, 4K resolution, or higher. For example, the WirelessHD specification is based on a 7 GHz channel in the 60 GHz Extremely High Frequency radio band. It allows either compressed or uncompressed digital transmission of high-definition video and audio and data signals. Other standards that may be applied are WIDI, Miracast™, Wireless Gigabit, Wireless HDMI, WHDI (Wireless Home Digital Interface), or other high-bandwidth WLAN or PAN standards.

In some embodiments, the distal and proximal interfaces, when coupled, define a rotatable connection that allows for independent rotation of the distal interface with respect to the proximal interface. Such rotation preferably rotates the entire distal portion 2702, the rotation including rotation about an axis that at least spans the distal and proximal interfaces when coupled together. The first RF channel and first RF receiver 2725 are respectively configured to maintain the RF communication channel between the first RF channel and the first RF receiver when the distal and proximal interfaces are coupled and the distal interface is rotated, with respect to the proximal interface, at least about the axis. Some embodiments may employ near-field communications in which the first RF modulator and the first RF antenna make up a low power, near-field radio transmitter, and first RF receiver and the second RF antenna make up a low power, near-field radio receiver.

Figure 32:
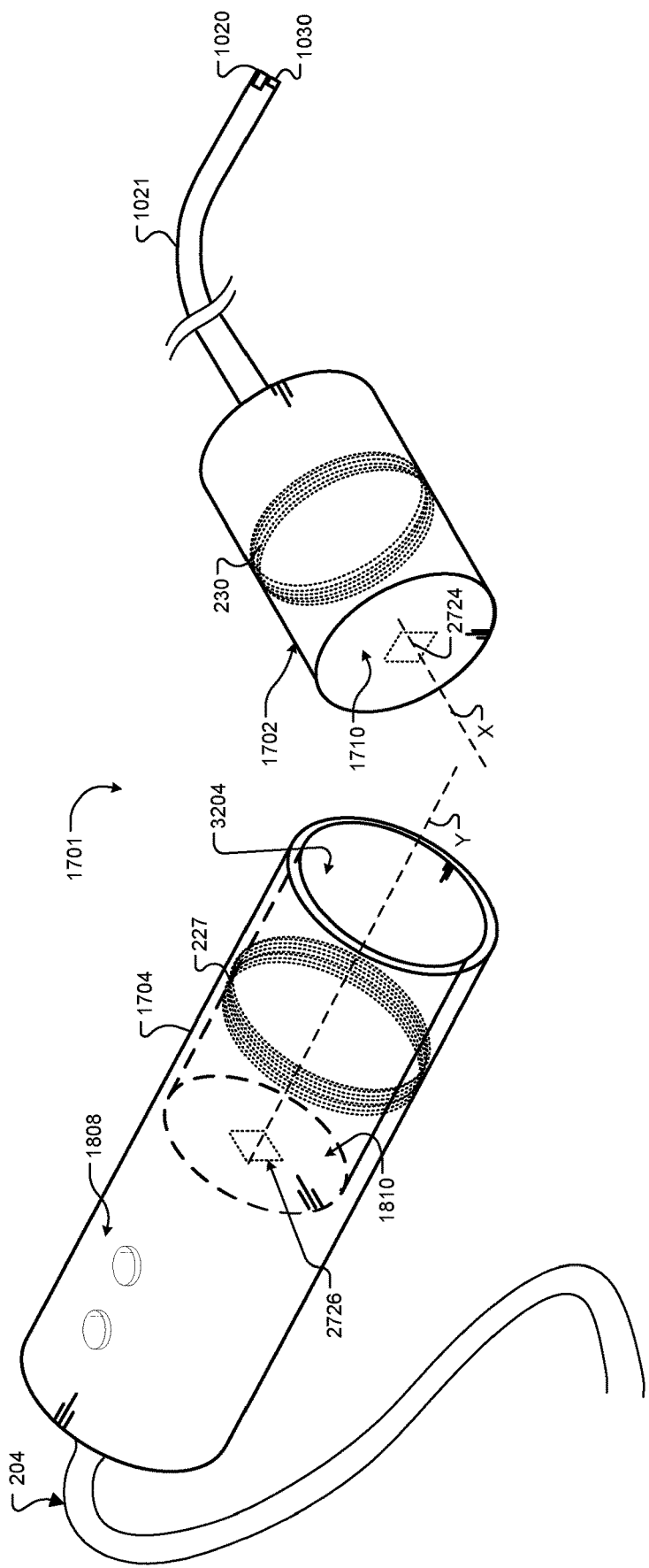
FIG. 32 is a perspective diagram of a video scope device according to another example embodiment employing RF video data transmission.

FIG. 32 is a perspective diagram of a video scope device according to another example embodiment employing RF video data transmission. The position of the power transfer elements and antennas is shown in the diagram. The internal electronics may be similar to those in FIG. 27 or 29, for example. In this embodiment, proximal portion 1704 includes a first receptacle 3204 into which the distal portion 1702 is adapted to be partially inserted to couple the proximal and distal portions. When inserted, the first antenna 2724, shown placed beneath the surface at the distal interface such that it sits opposite second antenna 2726 when the distal portion 1702 is inserted into the proximal portion 1704. The power transfer elements 227 and 230 are arranged similarly to the device of FIG. 18, with the various portions having similar reference numbers. The power transfer elements include an inductive coil positioned around an inside wall of the first receptacle 1804, and the power receiving element comprising an inductive coil positioned along an outer edge of the distal portion 1702.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

In the above descriptions and the following claims, terms such as top, bottom, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. A video medical scope defining an enclosed space between a first portion and a second portion, the video medical scope comprising:
 at least one image sensor for providing image data;
 a first interface arranged within the first portion comprising
  a first RF transmitter including a first RF antenna communicatively coupled to a first RF modulator that converts the image data to modulated image data;
  a first power transfer element for contactless transmission of electrical power across the enclosed space; and
 a second interface arranged within the second portion and configured to releasably couple to the first interface on opposite sides of the enclosed space, the second interface comprising
  a first RF receiver including a second RF antenna configured to receive the modulated image data from the first RF antenna;
  a second power transfer element for contactless transmission of electrical power when the first power transfer element is placed within a power coupling distance from the second power transfer element,
 wherein the first RF antenna comprises a short range low power RF antenna centrally located along an axis of rotation whereby the first interface and the second interface rotate with respect to each other, wherein the first RF transmitter is configured to transmit the modulated image data across the enclosed space to the first RF receiver when the first and second interfaces are coupled.

2. The scope according to claim 1, further comprising a second RF modulator arranged within the second portion, the second RF modulator adapted to communicate with a camera control unit (CCU) to modulate at least control data for the image sensor.

3. The scope according to claim 1, further comprising a first faraday cage structure positioned surrounding the first RF antenna in all directions excepting a first direction and a second faraday cage structure positioned surrounding the second RF antenna in all directions excepting a second direction opposite the first direction when the first and second interface are coupled.

4. The scope according to claim 1, wherein the first RF antenna is a directional antenna having a directional emission pattern directed toward the second antenna and the second RF antenna is a directional antenna having a directional emission pattern directed toward the first RF antenna when the first and second interfaces are coupled.

5. The scope according to claim 1, wherein the first RF modulator and the first RF antenna comprise a low power, near-field radio transmitter.

6. The scope according to claim 1, wherein the second portion includes a first receptacle into which the first portion is adapted to be partially inserted to couple with first and second portions, the first power transfer element comprising an inductive coil positioned along an outer edge of the first portion and the second transfer element comprising an inductive coil positioned around an inside wall of the first receptacle.

7. The scope according to claim 1, wherein the second power transfer element comprises a first flat inductive coil positioned in a radial extension of the second portion and the first power transfer element comprises a second flat inductive coil positioned in a radial extension of the first portion.

8. The scope according to claim 1, wherein the first portion contains an illumination light emitting device.

9. A video medical scope defining an enclosed space between a first portion and a second portion, the video medical scope comprising:
   at least one image sensor for providing image data;
   a first interface arranged within the first portion comprising
      a first RF transmitter including a first RF antenna communicatively coupled to a first RF modulator that converts the image data to modulated image data; and
      a first power transfer element for contactless transmission of electrical power across the enclosed space; and
   a second interface arranged within the second portion comprising
      a first RF receiver including a second RF antenna configured to receive the modulated image data from the first RF antenna; and
      a second power transfer element for contactless transmission of electrical power when the first power transfer element is placed within a power coupling distance from the second power transfer element;
   the first RF transmitter configured to transmit the modulated image data across the enclosed space to the first RF receiver when the first and second interfaces are coupled,
   the first RF antenna is a directional antenna having a directional emission pattern directed toward the second antenna and the second RF antenna is a directional antenna having a directional emission pattern directed toward the first RF antenna when the first and second interfaces are coupled.

10. The scope according to claim 9, further comprising a first faraday cage structure positioned surrounding the first RF antenna in all directions excepting a first direction and a second faraday cage structure positioned surrounding the second RF antenna in all directions excepting a second direction opposite the first direction when the first and second interface are coupled.

11. The scope according to claim 9, wherein the first RF modulator and the first RF antenna comprise a low power, near-field radio transmitter.

12. The scope according to claim 9, wherein the second portion includes a first receptacle into which the first portion is adapted to be partially inserted to couple with first and second portions, the first power transfer element comprising an inductive coil positioned along an outer edge of the first portion and the second transfer element comprising an inductive coil positioned around an inside wall of the first receptacle.

13. The scope according to claim 9, wherein the second power transfer element comprises a first flat inductive coil positioned in a radial extension of the second portion and the first power transfer element comprises a second flat inductive coil positioned in a radial extension of the first portion.

* * * * *